United States Patent
Chapman

(10) Patent No.: US 9,480,730 B2
(45) Date of Patent: Nov. 1, 2016

(54) METHOD AND APPARATUS FOR PREPARING SINGLE DONOR THROMBIN SERUM

(71) Applicant: Stem Cell Partners LLC, Sacramento, CA (US)

(72) Inventor: John R. Chapman, Sacramento, CA (US)

(73) Assignee: Stem Cell Partners LLC, Sacramento, CA (US)

( * ) Notice: Subject to any disclaimer, the term of this patent is extended or adjusted under 35 U.S.C. 154(b) by 0 days.

(21) Appl. No.: 14/413,222

(22) PCT Filed: Sep. 25, 2013

(86) PCT No.: PCT/US2013/061756
§ 371 (c)(1),
(2) Date: Jan. 6, 2015

(87) PCT Pub. No.: WO2014/052496
PCT Pub. Date: Apr. 3, 2014

(65) Prior Publication Data
US 2015/0182603 A1    Jul. 2, 2015

Related U.S. Application Data

(60) Provisional application No. 61/705,535, filed on Sep. 25, 2012.

(51) Int. Cl.
*A61K 38/48*  (2006.01)
*A61J 1/14*   (2006.01)
*A61K 35/16*  (2015.01)
*A61K 47/10*  (2006.01)

(52) U.S. Cl.
CPC .......... *A61K 38/4833* (2013.01); *A61J 1/1443* (2013.01); *A61K 35/16* (2013.01); *A61K 47/10* (2013.01); *C12Y 304/21005* (2013.01); *F04C 2270/0421* (2013.01)

(58) Field of Classification Search
CPC ................................................ A61K 38/4833
See application file for complete search history.

(56) References Cited

U.S. PATENT DOCUMENTS

| | | |
|---|---|---|
| 5,449,375 A | 9/1995 | Makower et al. |
| 5,585,007 A | 12/1996 | Antanavich et al. |
| 5,643,192 A | 7/1997 | Hirsh et al. |
| 5,733,545 A | 3/1998 | Hood, III |
| 5,759,171 A | 6/1998 | Alcone et al. |
| 5,779,660 A | 7/1998 | Halpern et al. |
| 6,048,966 A | 4/2000 | Cederholm-Williams et al. |
| 6,159,232 A | 12/2000 | Nowakowski |
| 6,214,338 B1 | 4/2001 | Antanavich et al. |
| 6,274,090 B1 | 8/2001 | Coelho et al. |
| 6,368,298 B1 | 4/2002 | Beretta et al. |
| 6,444,228 B1 | 9/2002 | Baugh et al. |
| 6,472,162 B1 | 10/2002 | Coelho et al. |
| 6,527,749 B1 | 3/2003 | Roby et al. |
| 6,544,162 B1 | 4/2003 | Van Wie et al. |
| 6,719,901 B2 | 4/2004 | Dolecek et al. |
| 6,830,762 B2 | 12/2004 | Baugh et al. |
| 6,921,380 B1 | 7/2005 | Epstein et al. |
| 6,942,880 B1 | 9/2005 | Dolecek |
| 7,029,430 B2 | 4/2006 | Hlavinka et al. |
| 7,045,585 B2 | 5/2006 | Berry et al. |
| 7,056,722 B1 | 6/2006 | Coelho et al. |
| 7,520,402 B2 | 4/2009 | Ellsworth et al. |
| 7,694,828 B2 | 4/2010 | Swift et al. |
| 7,767,452 B2 | 8/2010 | Kleinsek |
| 7,838,039 B2 | 11/2010 | Baugh et al. |
| 8,105,580 B2 | 1/2012 | Fraser et al. |
| 8,187,475 B2 | 5/2012 | Hecker et al. |
| 8,337,711 B2 | 12/2012 | Dorian et al. |
| 8,337,834 B2 | 12/2012 | Fraser et al. |
| 8,348,823 B2 | 1/2013 | Rochat |
| 8,529,957 B2 | 9/2013 | Turzi et al. |
| 8,586,324 B2 | 11/2013 | Leach et al. |
| 2004/0120942 A1 | 6/2004 | McGinnis et al. |
| 2006/0178610 A1 | 8/2006 | Nowakowski |
| 2008/0044852 A1 | 2/2008 | Kanayinkal et al. |
| 2012/0282240 A1 | 11/2012 | Overholser et al. |

FOREIGN PATENT DOCUMENTS

| | | |
|---|---|---|
| EP | 1198242 B1 | 5/2008 |
| WO | 9945938 | 9/1999 |
| WO | 0007659 | 2/2000 |
| WO | 0074713 | 12/2000 |
| WO | 2004058943 A3 | 7/2004 |
| WO | 2011110948 A2 | 9/2011 |

OTHER PUBLICATIONS

Rock, et al. Transfusion Medicine, 2007, 17, 187-191, Preparation and characterization of human thrombin for use in a fibrin glue (2007).
Oh DS, Cheon YW, Jeon YR, Lew DH, Activated platelet-rich plasma improves fat graft survival in nude mice: a pilot study. Dermatol Surg. 2011;37:619-625.

*Primary Examiner* — Bin Shen
(74) *Attorney, Agent, or Firm* — Temmerman Law Office; Mathew J. Temmerman

(57) ABSTRACT

A method for preparing thrombin serum, the method comprising obtaining blood fluid sample, contacting a first aliquot of the blood fluid with a procoagulant agent to form prothrombinase enzyme complex bound to the surface of the procoagulant agent so as to obtain an activated procoagulant agent that may be stored. The activated procoagulant agent may then be contacted with a second aliquot of the blood fluid containing prothrombin so as to obtain thrombin serum, which may be extracted and contacted with fibrinogen to obtain fibrin.

15 Claims, 10 Drawing Sheets

METHOD AND APPARATUS FOR PREPARING SINGLE DONOR THROMBIN SERUM

RELATED APPLICATIONS

This application claims priority under 35 U.S.C. §371 to PCT application No. PCT/US2013/061756, filed Sep. 25, 2013, which claims benefit to U.S. Provisional Patent Application 61/705,535, filed Sep. 25, 2012. These patent applications are incorporated herein in their entirety as if set out in full.

BACKGROUND OF THE DISCLOSURE

1. Field of the Disclosure

The invention relates to the conversion of prothrombin present in a blood fluid into thrombin, and more particularly to an apparatus and method for increasing the concentration of activated cascade coagulation proteins in blood.

2. Description of the State of the Art

Blood plasma coagulation is thought to occur through a series of interconnected self-amplifying, zymogen-enzyme conversions (FIG. 1) that penultimately produce thrombin (FIIa), a powerful serine protease. Dubbed the "coagulation cascade", in the final steps, prothrombin is converted to thrombin by a multi-protein complex with calcium called the prothrombinase enzyme complex. Thrombin is an enzyme that hydrolyses fibrinogen into fibrin units that polymerize into a fine mesh, which, in turn, causes plasma to form a gel or clot. Thrombin is a serine protease of the trypsin family with a molecular weight of approximately 34 kDa. It consists of two polypeptide chains.

The coagulation cascade is usually divided into two branches for convenience of discussion and coagulopathy testing. The intrinsic and extrinsic branches can be separately potentiated but merge into a common pathway leading to thrombin. The extrinsic pathway is responsible for hemostatic control and response to vascular injury. The intrinsic pathway starts when blood comes into contact with procoagulant materials, causing Factor XII activation. The contact activation of blood plasma coagulation by procoagulant materials has been well studied as in J Biomed Mater Res. 1995 August; 29(8):1005-16 and J Biomed Mater Res. 1995 August; 29(8):1017-28, the entire contents of which are incorporated herein by reference.

Procoagulant refers to any element or activity that causes the blood fluid to form a thrombin mediated fibrin clot. Procoagulant agents include a variety of negatively charged surfaces, including organic and inorganic materials including kaolin, cotton, ceramic, glass, ellagic acid and the like. Procoagulant agents are known to be used singularly or in combination.

Binding to these negatively charged surfaces induces a conformational change in Factor XII (FXII) that allows it to proteolytically activate prekallikrein (PK). PK proteolytically activates FXII, producing a positive feedback loop that amplifies the system and leads to activation of FXI and cleavage of high-molecular-weight kininogen (HK) by kallikrein.

A subsequent product of Factor XIIa activation by procoagulant materials is the formation of the prothrombinase enzyme complex that consists of the serine protease, Factor Xa, and the protein cofactor, Factor Va. The complex assembles on negatively charged phospholipid membranes in the presence of calcium ions. The addition of calcium salt to citrate anti-coagulated blood fluids to enable the coagulation cascade to proceed is often specifically referred to as recalcification. The prothrombinase enzyme complex catalyzes the conversion of prothrombin (Factor II), an inactive zymogen, to thrombin (Factor IIa), an active serine protease. Although it has been shown that Factor Xa can activate prothrombin when unassociated with the prothrombinase enzyme complex, the rate of thrombin formation is severely decreased under such circumstances.

The important blood factors involved in coagulation that circulate in normal blood are present in much lower concentration than a plethora of other blood proteins (about 490 of them at concentrations varying over six decades). Among many unresolved issues, one is the manner in how high-concentration blood proteins such as albumin, fibrinogen, or IgG fail to compete with assemblage of activation-complex proteins at procoagulant surfaces that are composed of proteins at considerably lower blood concentrations (referred to an "adsorption-dilution" effect). Zhuo et al., Biomaterials. 2007 October; 28(30): 4355-4369, the entire contents of which are incorporated herein by reference, discloses the rate of FXIIa accumulation in whole-plasma is found to decrease with time in the continuous presence of activating surfaces, leading to a steady-state FXIIa yield dependent on the initial FXII solution concentration for procoagulant particles suspended in plasma. The authors explain that the results strongly suggest that activation competes with an autoinhibition reaction in which FXIIa itself inhibits FXII→FXIIa. Erwin A. Vogler and Christopher A. Siedlecki, Biomaterials. 2009 April; 30(10): 1857-1869, the entire contents of which are incorporated herein by reference, have comprehensively reviewed the additional uncertainties that exist in contact activation coagulation chemistries including autoactivation, autohydrolysis, and autoinhibition reactions. See generally, FIG. 1.

Prothrombinase enzyme complex assembly begins with the binding of Factor Xa and Factor Va to negatively charged phospholipids on plasma membranes. Once bound to the plasma membrane, Factor Xa and Factor Va rapidly associate in a 1:1 stoichiometric ratio to form the prothrombinase enzyme complex. The assembly of the prothrombinase enzyme complex is calcium dependent. The fully assembled prothrombinase enzyme complex catalyzes the conversion of the zymogen prothrombin to the serine protease thrombin. When associated with the prothrombinase enzyme complex, the catalytic efficiency of Factor Xa is increased 300,000-fold.

The coagulation system is under extraordinarily tight regulation by both stoichiometric and dynamic inhibition systems. The concentrations of plasma procoagulants, the stoichiometric inhibitors, and the constituents of the dynamic inhibition processes largely regulate the ultimate amount of thrombin produced. For example, Factor Va of the prothrombinase enzyme complex is inactivated following cleavage by activated protein C, which reduces the ability of Factor V to bind to Factor Xa. Factor Xa of the prothrombinase enzyme complex is inhibited by the antithrombin III, which also acts to inhibit thrombin. Thrombin in plasma is only transiently stable having a half-life of approximately 10-15 seconds largely through the inhibitory properties of the plasma protein antithrombin III (Advanced Engineering Materials Volume 11, Issue 12, pages B251-B260, December, 2009, the entire contents of which are incorporated herein by reference.)

The exact chemistry of autoactivation, autohydrolysis, and autoinhibition reactions of the coagulation system remain unknown. Resolution of an improved reaction scheme for contact activation may require a solution to vexing problems of protein adsorption and protein-adsorption competition, as well as a greatly improved understanding of the biochemistry involved in surface activation of zymogens.

The role of thrombin in the coagulation cascade and its use for bioengineering applications of fibrin gels has been reviewed, for example by Janmey et al., J. R. Soc. Interface (2009) 10, 1-10, the entire contents of which are incorporated herein by reference. Thrombin is used clinically to control bleeding during surgery, for burns and in certain trauma situations. Bovine thrombin is also a component of some commercial tissue glues.

Conventional commercial thrombin therapeutics are purified from pooled human and animal blood products and as such run the risk of contamination with viruses such as the HIV and hepatitis viruses. In comparing three commercial thrombin preparations, Suzuki and Sakuragawa found that the preparations contained contaminating proteins, and the human preparation contained immunoglobulin G, hepatitis B surface antigen antibodies and human immunodeficiency antibodies. Xenogeneic immunization with bovine thrombin has been reported in patients who have developed self-reactive antibodies to both human thrombin and human factor V (factor V is a contaminant in the bovine thrombin preparation). In addition, concerns have recently been raised regarding the possible contamination of bovine products with pathogens such as the bovine spongiform encephalitis agent, which is not detectable or inactivated by conventional means. Therapeutic human blood products are also subject to contamination by viral particles such as the hepatitis virus and the human immunodeficiency virus. There are also cultural and religious reasons that bovine thrombin is not found to be acceptable for clinical use.

Recombinant thrombin has recently been approved by the FDA and is being promoted commercially as an alternative to bovine plasma-based thrombin, which can potentially cause the formation of inhibitory antibodies to bovine thrombin, and other safety concerns associated with an animal-derived blood product. However, recombinant thrombin has also been demonstrated to have immunogenicity issues in some patients who received the product.

It has long been understood, however, that the safest condition for a surgical patient in need of a fibrin sealant would result from a two component biological sealant preparation in which the thrombin component would be harvested from the same donor in which the fibrinogen protein component was harvested-forming a fully autologous biological sealant or glue so as to avoid any risk of blood borne disease transmission.

The concept of utilizing thrombin and/or fibrinogen sourced from the patient in a medical procedure performed on that patient dates to 1974 and is not novel. Cederholm-Williams PCT Patent (WO94/00566-10 Jan. 1994) describes an improved fibrin glue in which the thrombin component, which required thirteen steps, including centrifugation, and separation of intermediate precipitates and adjusting the ionic strength of the blood and pH of the plasma to prepare, would be combined with a fibrinogen component also sourced from the plasma of the same donor. However, these many preparation steps are so time consuming they become impractical for use in the perioperative theater where processing times should be less than one hour.

Three years later, in 1997, Hirsh, et al. (U.S. Pat. No. 5,643,192) follows Cederholm-Williams by teaching another method of preparing fibrin glue in which both the fibrinogen and thrombin components of a fibrin glue are sourced from the same donor's plasma. The Hirsh patent describes a method of preparing thrombin in which most of the fibrinogen in the plasma is first precipitated and removed to prepare a supernatant and then clotting the residual fibrinogen in the supernatant which is different and simpler than the method taught by Cederholm-Williams, but does not result in a commercially useful thrombin in that the thrombin provides clotting speeds of five seconds or less for only 4 minutes, and less than 10 seconds for only 47 minutes.

These clotting speeds are unsuitable to the needs of surgeons who could not plan their entire surgeries around the limitations of the Hirsh, et al. fibrin glue.

Surgeons predominately require a fast acting clotting time (<5 seconds) for hemostasis and tissue sealing or adhesion. Slow clotting biological glues (>5 seconds) will often be transported away from the wound site by oozing and bleeding before they can perform their function. A surgeon utilizing the Hirsh fibrin glue would be required to arrange his surgery so that the hemostasis and tissue sealing intended for treatment with the Hirsh fibrin glue would occur within the 4 minute window where the clotting time was less than 5 seconds, making the Hirsh invention totally impractical for most surgeries which predominantly require rapid hemostasis and tissue adhesion throughout the surgery, the time span of which could extend to six hours.

Sternberger discloses in Br J Exp Pathol. 1947 June; 28(3): 168-177, the entire contents of which are incorporated herein by reference, that ethanol can be used to stabilize thrombin activity in plasma. Coelho et al. in U.S. Pat. No. 7,056,722, the entire contents of which are incorporated herein by reference, disclose an invention for a simple, practical, and fast method of preparing stable human thrombin from a donor's blood using ethanol as a thrombin stabilizing agent. The method provides fast clots (less than 5 seconds) that are stable throughout a lengthy surgery (e.g., six hours) by the addition of ethanol at a concentration of 8% to 18%. Coelho et al. further teaches that an apparatus for manufacturing a thrombin preparation from blood that is not stabilized with ethanol is totally impractical for the broad range of surgeries in which thrombin is used. The inventors had to identify the very narrow range of ethanol concentration that was sufficiently low to avoid inhibition of the coagulation cascade which would prevent generation of the thrombin but sufficiently high enough to stabilize thrombin.

Kumar et al. disclose in JECT 2005; 37:390-395 and in JECT. 2007; 39:18-23, the entire contents of which are incorporated herein by reference, teaches that the easiest way to initiate thrombin production is to add calcium ions to citrated plasma. Here, the surplus calcium allows the clotting cascade to initiate and thrombin to be produced. Kumar further teaches that the disadvantage with this procedure is that the stability of the thrombin activity in the produced thrombin is short, and because of the inhibition of the coagulation cascade by Protein S, Protein C and anti-thrombin III, the activity is typically decreased to a non-functional state within 20 minutes of production. Kumar et al. further disclose a method and device to circumvent these limitations in which a stable thrombin product may be produced when the inhibitory enzymes are partially inactivated using ethanol. To concentrate and activate thrombin, a mixture of calcium chloride and ethanol is added to citrate anti-coagulated plasma in the presence of a negatively charged surface. The negatively charged surface initiates the formation of the prothrombin-FV-FXa complex, whereas the mixture of calcium chloride and ethanol (the thrombin reagent) provides the chemical constituents to inactivate inhibitors of thrombin and to partially stabilize the thrombin so that it can be used hours after production. Kumar and Chapman in JECT. 2007; 39:18-23, the entire contents of which are incorporated herein by reference, also disclose a method to generate autologous human thrombin from whole blood instead of plasma as the starting source biologic fluid within a 30-minute period, however, like much of the other prior art, it still employs ethanol as an additive to stabilize the thrombin product however with thrombin activity continuously decaying over time even with storage at 4° C.

Thrombin serum/ethanol preparations such as those disclosed in Coelho et al. in U.S. Pat. No. 7,056,722 and Kumar are not biocompatible solutions as disclosed by Semple et al. in J Oral Maxillofacial Surg 66:632-638, 2008, the entire contents of which are incorporated herein by reference. The preparations are cytotoxic unless substantially diluted prior to administration to a final ethanol concentration of less than 4%.

The use of ethanol as a stabilizer for thrombin is also disclosed in McGinnis et al. in U.S. Pat. Pub. 2004/0120942, the entire contents of which are incorporated herein by reference. McGinnis et al. also disclose the use of "contact activation agents," which are meant to be agents involved in the intrinsic pathway of coagulation, and includes but is not limited to glass, glass beads, diatomaceous earth, ceramics, kaolin and any combination thereof.

Kanayinkal et al. in U.S. Pat Pub. 2009/0044852, the entire contents of which are incorporated herein by reference, disclose contacting the thrombin composition with a stabilizing agent to provide a thrombin composition having a stable-life of more than about 10 hours wherein the stabilizing agent comprises ethanol in a range of 8% to 25%, a polyol, PEG, ammonium sulfate, a non-polar solvent, a polar solvent, a methyl isobutyl ketone alcohol, glycol, tricloroacetic acid, acetate salt, or any combination thereof. While this system does provide an extended-life thrombin producing composition, biocompatibility complications may be introduced due to the presence of the stabilizing agent.

Nowakowski in U.S. Pat. No. 6,159,232 issued on Dec. 12, 2000; in U.S. Pat. No. 6,478,808 issued on Nov. 12, 2002; in U.S. Pat. No. 6,482,223 issued on Nov. 19, 2002 and U.S. Pat. No. 6,989,022 issued on Jan. 4, 2006 and in US Pat. Pub. No. 2006/0178610 published on Aug. 10, 2006, the entire contents of all of which are incorporated herein by reference, discloses a wound closure method and apparatus wherein the clotting cascade of a blood fluid is first initialized while the fluid is outside the body and within a substantially enclosed sterile container. The clotting cascade initiation apparatus may include a procoagulating agent (a component capable of causing blood fluid to form a clot), mechanisms to substantially neutralize an anticoagulant (such as adding liquid protamine sulfate to the blood fluid so as to inhibit the anticoagulant heparin), or a mechanism to substantially neutralize an anticlot (examples of anticlot inhibitors are described as tranexamic acid and plasminogen binding material). The clot-activated blood fluid is then deposited about the wound wherein the clotting continues.

Recently, the importance of thrombin beyond its key role in the clotting process has been investigated. Bae et al. in J Cell Physiol. 2009; 219(3): 744-751, the entire contents of which are incorporated herein by reference, reviews that thrombin, in addition to playing a central role in the formation of blood clots by cleaving fibrinogen to fibrin, possesses diverse biological activities related to inflammation, allergy, tumor growth, metastasis, apoptosis, and tissue remodeling. Thrombin's ability to modulate a variety of cell functions is achieved in m any cases through the interaction with specific cell surface receptors. All of the known thrombin receptors belong to the protease-activated receptor (PAR) family and are characterized by a peculiar proteolytic mechanism of activation. Receptor activation occurs when thrombin cleaves the extracellular domain of the receptor exposing a tethered ligand. Among the receptors of the PAR family, thrombin can interact specifically with PAR-1, -3, and -4. Additionally thrombin is a powerful mitogenic agent for some cells.

Despite this progress, the ideal method of manufacturing single donor thrombin serum at the point of care remains lacking. The ideal thrombin preparation apparatus and method must be safe to use within the body and should therefore be derived from the patient's own blood and should not require cytotoxic additives such as ethanol to overcome thrombin stability issues.

The above prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

SUMMARY OF THE INVENTION

It is an object of the present invention to provide a new and improved method and apparatus for the preparation of thrombin serum. Other objects and advantages will be apparent to the person skilled in the art after reading the specification and claims hereof. The present invention better addresses the unmet need for a simple, practical, rapid means of preparing safe and effective thrombin serum for medical applications from the blood fluid of a single donor at the point of care. A method and apparatus for the preparation of thrombin serum is disclosed wherein thrombin serum can be made from blood fluids in a rapid and repetitive manner upon demand of the treating physician. The present invention teaches a two stage method of obtaining thrombin serum form a blood fluid. In the first stage, a procoagulant agent is converted to activated procoagulant agent by means of obtaining prothrombinase enzyme complex on the surface of the procoagulant agent. The prothrombinase enzyme complex is derived from coagulation proteins present in a blood fluid. In the second stage, which can be temporally performed upon demand of the operator, thrombin is obtained from prothrombin by contacting the activated procoagulant agent with a biological fluid comprising coagulation proteins including prothrombin. Because these coagulation pathway reactions are calcium dependent, a suitable concentration of calcium ions must be provided to the reaction mixtures. The invention further teaches an apparatus for containing the reaction mixtures as well as addition and extraction means of fluid transfer.

For the purpose of the present invention, a procoagulant agent is a material that has the capacity to activate the blood system's coagulation cascade to at least the point of obtaining thrombin production and preferably to the point of obtaining fibrin (FIG. 1). A preferred procoagulant will be presented to the blood so as to have a high surface area which is best achieved by using procoagulant particles having a diameter of less than 5 mm or being porous particles. The activation step is achieved by contacting the procoagulant agent with a first blood fluid aliquot in the presence of free calcium ions. While not wishing to be bound by theory, it is believed that at the molecular level, the first stage activation of the apparatus is due to prothrombinase enzyme complex being generated on the surface of the procoagulant agent in a meta-stable form. Activation of the apparatus requires only about five to ten minutes with a blood fluid. The activation state persists at a high level for at least ten hours before gradually decaying to inactive levels by twenty-four hours. This duration of sustained activation state is attributed to the prothrombinase enzyme complex having this duration of functional stability which is both surprising and unpredictable considering how short the half life of other elements of the coagulation cascade persist to avoid excessive clotting of blood. Ten hours of maintained procoagulant activation is fortuitous as it is a time period longer than most surgeries. Once activated, the apparatus can be used to rapidly (e.g., about 1 minute) prepare medically useful amounts of thrombin from a second blood fluid aliquot added to the apparatus. The rapid production of thrombin is attributed to the large numbers of prothrombinase enzyme complexes formed on the high surface area of the procoagulant agent catalyzing the conversion of prothrombin to thrombin. The rapidity at which thrombin is formed far exceeds the rate at which thrombin neutralizing agents such as anti-thrombin III can neutralize thrombin due to the difference in the kinetics of the prothrombinase enzyme complex reaction versus the thrombin and anti-thrombin III forming an inactive complex reaction kinetics. This difference in kinetics between thrombin production and thrombin neutralization creates a time window for the ability to have clinically useful amounts of thrombin available. The more rapid the thrombin production that can be achieved (e.g., the more prothrombinase enzyme complexes formed), the greater the duration of time of clinically useful amounts of thrombin will exist in the thrombin serum. Further, it was learned through experimentation that the reaction kinetics of the thrombin and anti-thrombin III are much more temperature sensitive (inhibited by temperatures <10° C.) than the production of thrombin so even useful amounts of thrombin can be stored using chilled blood products and that the useful shelf life of the formed thrombin serum can be significantly improved by cold storage. The present invention therefore enables the rapid production of biocompatible thrombin serum from the patient's own blood on demand of the surgical team. The invention further teaches a means for the apparatus to be used repetitively meaning a second, third, fourth, and so on blood aliquot can be added to the same apparatus in the same manner to generate a additional independent aliquots of thrombin serum. Further, the present invention teaches that each use of the apparatus to prepare thrombin serum causes the activation state of the procoagulant agent to be renewed for an additional ten hours enabling the operator to continue to have continuous rapid thrombin production from a single device. The economic value and potential for cost-savings derived by enabling large volume thrombin production using the patient's own blood fluid at the point of care is another beneficial aspect of the present invention.

Plasma is the acellular fraction of blood and includes numerous proteins including proteins of the coagulation cascade and fibrinogen. When fibrinogen is converted to fibrin by the action of thrombin, the plasma becomes greatly reduced in fibrinogen concentration and is designated as serum instead of plasma. For the purpose of the present invention, thrombin serum is used as a term to describe any biological fluid that contains detectable thrombin enzyme clotting activity of converting fibrinogen into fibrin regardless of its cellular content. For the purpose of the present invention, a blood fluid is a term used herein to describe a biological fluid derived from a donor having a functional capacity to generate prothrombinase enzyme complex upon activation of the coagulation cascade and is selected from a list comprising whole blood, citrate anti-coagulated whole blood or plasma, or any other suitable blood fraction matter having prothrombin as a constituent, plasma including platelet rich plasma, buffy coat rich plasma, platelet poor plasma, whole bone marrow, citrate anti-coagulated bone marrow, whole cord blood, citrate anti-coagulated bone marrow and any other coagulation cascade competent blood fluid preparations. Further, the present invention teaches that different blood fluids can be used in the same apparatus. By means of non-limiting example, the first stage of the activation of the procoagulant agent can be achieved by adding whole blood to the apparatus and for the second stage of generating thrombin serum, the blood fluid employed could be a different blood fluid such as platelet rich plasma.

The present invention as disclosed in greater detail hereinafter and as particularly claimed was discovered by a number of unexpected, non-predictable and surprising experimental observations including: 1) that prothrombinase enzyme complex once formed on the high surface area of the preferred procoagulant agent during the initial minutes of mixing blood fluid, calcium with the procoagulant agent in the apparatus remains in a persistent functional state of sustained enzymatic activity to be able to facilitate the rapid conversion of prothrombin to thrombin for a clinically useful period of time of at least six hours but less than twenty-four hours thereby enabling "on demand" thrombin preparation from a stored activated apparatus; 2) the discovery that thrombin can be generated abundantly and very rapidly, within seconds instead of minutes, upon contact of a blood fluid prothrombin source with an activated procoagulant agent and thereby enables clinically useful concentrations of thrombin to be reliably achieved faster than possible before (e.g., a 1 minute incubation) further enabling "on demand" thrombin preparation from stored activated apparatus; 3) the discovery that storing the harvested thrombin serum at <10° C. significantly enhances thrombin stability without ethanol being present as stabilizer as disclosed by Kumar et al. 2007 further supporting the practicality of the "on demand" approach for preparing biocompatible thrombin serum; 4) the discovery that a single apparatus can be used repetitively for generating multiple batches of thrombin and that each thrombin production further serves also to maintain the procoagulant agent within the apparatus in an activated state for at least an additional 10 hour period further supporting the commercial viability of an apparatus as a single apparatus can be used for producing large amounts of fresh thrombin serum from a single donor; 5) the discovery that eliminating ethanol from the blood fluid as taught by the prior art for preparing single donor thrombin enables more rapid activation of the procoagulant such that only 10 minutes of time is required to have the capability to produce clinically useful thrombin instead of the 30 to 60 minutes required when ethanol is added to the blood fluid as taught by the prior art enabling more rapid single donor thrombin availability to the patient, 10) the discovery that the addition of ethanol at a concentration of 18% to 25% v/v to the blood fluid can still be employed to stabilize thrombin if so desired by adding the ethanol after the first activation of the procoagulant has been achieved so as to improve on the prior art which suffers from being slow and unreliable production of thrombin due to ethanol having to be present in precise concentrations to avoid degradation of the coagulation cascade (excessive ethanol concentration) or to avoid failure to stabilize thrombin (insufficient ethanol concentration).

The present invention discloses a means to repetitively use and store a single apparatus that has been activated by a first blood fluid aliquot contact in the presence of calcium ions so as to greatly accelerate the availability and amount of thrombin contained in one or more thrombin preparations made on demand over a 10 hour period by contact with one or more additional blood fluid aliquots. The transiently stable thrombin produced by the present invention is done so without the use of thrombin stabilizing additives. Accordingly, the preferred embodiment of the invention ameliorates or overcomes one or more of the significant shortcomings of the prior art by disclosing a practical method for producing clinically useful thrombin preparations on demand from a blood fluid which is selected from the list comprising blood, single donor whole blood, plasma, pooled plasma, platelet rich plasma, platelet poor plasma or a whole blood fraction including plasma having the coagulation cascade intact (herein designated as blood fluid). Dramatic improvements may be realized by practicing the invention for preparing thrombin in regard to control, efficacy, reliability, safety, and cost performance. Specifically, the method and apparatus disclosed enables through the use of a single apparatus the rapid, reproducible, repetitive and planned production of abundant clinically useful thrombin preparations from readily available biologic fluids for achieving hemostasis, promoting wound healing, or delivering cell compositions in a manner that is easy to perform by a person of ordinary skill throughout the duration of long surgeries. The invention further provides a method of using the thrombin serum preparation to conveniently practice the method by providing an apparatus to carry out the method.

The procoagulant agent is preferably selected from the list comprising but not limited to glass, glass beads, glass fibers, ceramic, ellagic acid, and diatomaceous earth or the like that is associated with a functional prothrombinase enzyme complex and defined as activated procoagulant. The preferred procoagulant agent is borosilicate glass beads having a diameter of between 50 microns and 2 mm, such that they are easily retained within the reaction chamber whilst allowing blood cells to pass (approximately 6-10 micron diameter) by means readily known to those skilled in the art such as filter screen, depth filters, and the like. It is advantageous to provide a large surface area for the procoagulant agent to lie on the bottom of the reaction chamber. It is particularly advantageous to include in the reaction chamber other detached objects having a larger diameter and greater mass to be used for triturating formed fibrin gels by physical agitation such as manually shaking the apparatus. Exemplary suitable detached objects are 6 to 8 mm beads prepared from medically acceptable materials for blood contact such as glass, polystyrene, polycarbonate and polyethylene, although it should be readily understood that other means for triturating formed fibrin gels may be utilized. Preferably, all portions of the apparatus are biocompatible with human use and may withstand sterilization by one or more known sterilizing methods including gamma irradiation, e-beam or less preferably ethylene oxide gas.

It was unexpected and surprising that despite the presence of prothrombinase enzyme complex inhibitors (anti-thrombin III and activated Protein C and Protein S) and abundant amounts of other adsorbing proteins such as albumin and immunoglobulin in the reaction mixture, that sufficient stability of the prothrombinase enzyme complex was maintained over a prolonged period of time. However, this heightened thrombin production chemistry was not permanent and expired within 24 hours of storage at room temperature. Noting that the reasons for the prolonged stability are unknown and surprising given how quickly most activated coagulation proteins expire due to the checks and balances of the coagulation system, no scientific evidence exists to enable one skilled in the art to predict without experimentation that such enabling stability timeframes would be discovered. One skilled in the art would not be able to predict a stability of at least 10 hours but less than 24 hours to occur.

The present invention provides an a apparatus that is simple to use, handheld, inexpensive, and reliable apparatus for use at the point of care preferably with a single donor or preferably an autologous source of blood fluid (See FIGS. 4-6).

The present invention provides physicians a thrombin preparation that is safer for the recipient of the thrombin preparation as compared to existing thrombin products. The first means of improved safety is that the present invention reduces the risk associated with existing thrombin preparations by avoiding the addition of chemical adulterants such as cytotoxic concentrations of ethanol as stabilizing agents. The absence of such chemical additives is particularly valuable as it eliminates the risk of a chemical toxic response when the thrombin preparation is applied to the recipient. As a second means of improved safety, the thrombin preparation described in the present invention is not derived from a different species as is the case for bovine thrombin or genetically modified hamster cell lines thereby avoiding the risk of pathogen transmission and immunogenic reactions. As a third means of improved safety, the present invention enables the thrombin preparation to be derived from a single donor rather than from pools of plasma from potentially hundreds or even thousands of donors as is currently practiced, thereby mitigating the risk of transmitting infectious diseases remaining in the pooled product. As a fourth means of improved safety, the thrombin preparation is simple and rapid enough that it may be prepared at the point of use, thereby enabling a patient's own blood fluid to be used to prepare the thrombin. Autologous blood products are universally recognized as the safest biologic preparations. As a fifth means of improved safety, the present method and apparatus are sufficiently simple that they can be utilized within the sterile field of the operating room, thereby avoiding the need to transfer materials out and then back into a sterile field and thereby avoiding an increased risk of microbial contamination of the sterile field, and ultimately an increased risk that the patient acquires a nosocomial infection.

The thrombin produced according to the method of the present invention is useful for the same conventional therapeutic applications of thrombin as is known and was recently reviewed in Ham et al., Journal of Blood Medicine 2010:1 135-142, the entire contents of which are incorporated herein by reference. The present invention provides a means for producing a thrombin preparation that has a sufficient concentration of thrombin at the time of use as to be efficacious for the intended purpose of producing fibrin from fibrinogen. The present invention is particularly well suited for the generation of fibrin gels for the delivery of cells such as platelets and stem cells. The addition of thrombin preparations to platelet rich plasma to form platelet rich gels is widely used in the practice of medicine as recently reviewed by Akingboye et al., AA, J Extra Corpor Technol. 2010 March; 42(1):20-9, the entire contents of which are incorporated herein by reference.

The method and materials described for producing the disclosed thrombin preparation are practical because they are rapid, reliable and easy to use such that they may be used in a variety of different circumstances spanning from the intra-operative theatre, point of care or in a laboratory setting or by users which have varying capabilities of know-how and are within the skill of an operating nurse to perform. Further, the present apparatus and method minimizes the amount of hands-on time and total time from start to finish to about 10 minutes, which is a shorter time than other methods in current use. The present method does not require electromechanical devices such as centrifuges or heaters to be used to prepare the thrombin serum.

Nowakowski, Coelho, Kumar and the remaining prior art does not alone or in combination teach, suggest, or motivate: 1) the disclosed two stage process to make thrombin serum; 2) a practical means of overcoming thrombin serum instability by storing an activated procoagulant agent; 3). a means for the repetitive use of the activated procoagulant agent for preparing multiple batches of thrombin serum from a single device, or 4) the inclusion of a means for triturating fibrin gel formed within a reaction chamber to release thrombin serum from fibrin gel using detached objects.

In light of the deficiencies of the prior art, it is a primary object of the present invention to provide biocompatible thrombin serum from a single donor's blood fluid on demand without the required use of cytotoxic thrombin stabilizing chemicals in a process sufficiently simple so as to be performed by medical staff such as surgical nurses at the point of care.

It is a further object of the present invention to provide a practical method for preparing thrombin serum that has a minimum process time of about 10 minutes.

It is a still further object of the present invention to provide a biocompatible thrombin serum, which provides clotting in less than 10 seconds.

It is a still further object of the present invention to provide thrombin that may be sprayed through small orifices or expressed through thin tubes alone or in combination with a fibrinogen source.

It is a still further an object of the present invention to provide a method for preparing biocompatible thrombin, the method comprising: obtaining a first aliquot of blood fluid; adding sufficient $CaCl_2$ to the first aliquot of blood fluid to recalcify the blood fluid, adding a procoagulant agent, forming a first mixture there from, the forming steps comprising: transiently agitating the first composition to mix; storing the first composition for at least about 10 minutes and less than six hours; storing said first mixture for a period of time until thrombin serum is desired to be available; obtaining a second aliquot of blood fluid; adding sufficient $CaCl_2$ to the second aliquot of blood fluid to recalcify the blood fluid, adding the second aliquot containing $CaCl_2$ to the stored first mixture to create a second mixture composition; transiently agitating the second mixture composition to mix; incubating the second composition until a fibrin gel is formed, triturating the fibrin gel to release a thrombin serum; and filtering the thrombin serum to remove particulate, thereby passing the thrombin through a filter membrane having a pore size to enable fluid to thrombin serum flow but large enough to prevent passage of procoagulant agent (e.g., 20 micron pore size); storing the harvested thrombin serum at room temperature and more preferably on wet ice (<10° C.) and finally contacting the thrombin serum with a fibrinogen source to create fibrin.

It is a still further object of the present invention to provide a method for production of thrombin serum that is suitable for preparing a viable cell suspension incorporated into a fibrin gel for the purpose of preparing a tissue graft, for performing cell culture, for conducting a diagnostic test, or other purposes known in the art of combining cells and tissues with fibrin sealants. The importance of using biocompatible thrombin is especially important for preparing living cell composite grafts so as to maintain the viability of the cells contained in the fibrin graft.

It is a still further object of the present invention to provide an apparatus that can be repetitively used to extract the thrombin serum multiple times without the need for activation. Adding a 3rd, 4th or 5th or more aliquots of blood fluid to the apparatus can rapidly achieve this within 10 hours of the last addition of a prior blood fluid addition to the apparatus. Each blood fluid aliquot should be treated with CaCl2 solution to recalcify the blood fluid if a calcium-chelating agent such as sodium citrate was used as the anticoagulant. The present invention is not suitable for use with blood fluid that has been anti-coagulated with heparin unless steps taken as disclosed by Nowakowski to remove heparin from the blood fluid are employed.

The present invention provides an improved method to provide thrombin for medical use by overcoming the limitations illustrated by the efforts of other works in the field. The present invention provides thrombin at concentrations that will provide fast clots when combined with a fibrinogen source (<5 to 10 seconds) as needed throughout a lengthy surgery (e.g. ten hours). Previous works in the field (Hirsch, et al.) exemplified the problem that thrombin has only minimal stability in that the thrombin achieved rapid clotting of fibrinogen (i.e., less than 5 seconds) exist only in a very narrow four to five minute time period, or required so many steps and elapsed time it would not be suitable for perioperative preparation, both totally impractical for the broad range of surgeries. Previous efforts in the field (e.g., Coelho et al.) have attempted to overcome this limitation of short stability of thrombin serum by the addition of ethanol as a chemical stabilizer for thrombin but in so doing introduced a new biocompatibility issue due to the cytotoxic concentration of ethanol required for achieving improved thrombin stability.

Accordingly, the problem of thrombin instability is solved more perfectly in the present invention. By creating a two-stage process, an activated procoagulant agent can be made and stored until proximate the time thrombin serum is needed and thereby delaying the preparation of the thrombin serum so as to overcome thrombin's well known transient stability issue. The harvested thrombin preparation from the activated apparatus retains its rapid clotting capability for at least 15 minutes when stored at room temperature and for at least one hour when stored at <10° C. without the need for a chemical additive. By storing the activated apparatus instead of storing thrombin serum stabilized with ethanol as taught by the prior art of Coelho and Kumar and others, the present invention provides the means to more quickly provide clinically useful thrombin serum preparations with both rapid clot times (e.g., less than 10 seconds) that are biocompatible from a single donor at the point of care.

BRIEF DESCRIPTION OF THE FIGURES

The foregoing aspects and many of the attendant advantages of the invention will become more readily appreciated as the same becomes better understood by reference to the following detailed description, when taken in conjunction with the attached charts and figures, wherein.

DETAILED DESCRIPTION OF THE INVENTION

The following description is presented to enable a person of ordinary skill in the art to make and use various aspects and examples of the present invention. Descriptions of specific materials, techniques, and applications are provided only as examples. Various modifications to the examples described herein will be readily apparent to those of ordinary skill in the art, and the general principles defined herein may be applied to other examples and applications without departing from the spirit and scope of the invention. Thus, the present invention is not intended to be limited to the examples described and shown, but is to be accorded the scope consistent with the appended claims.

Figure 1:
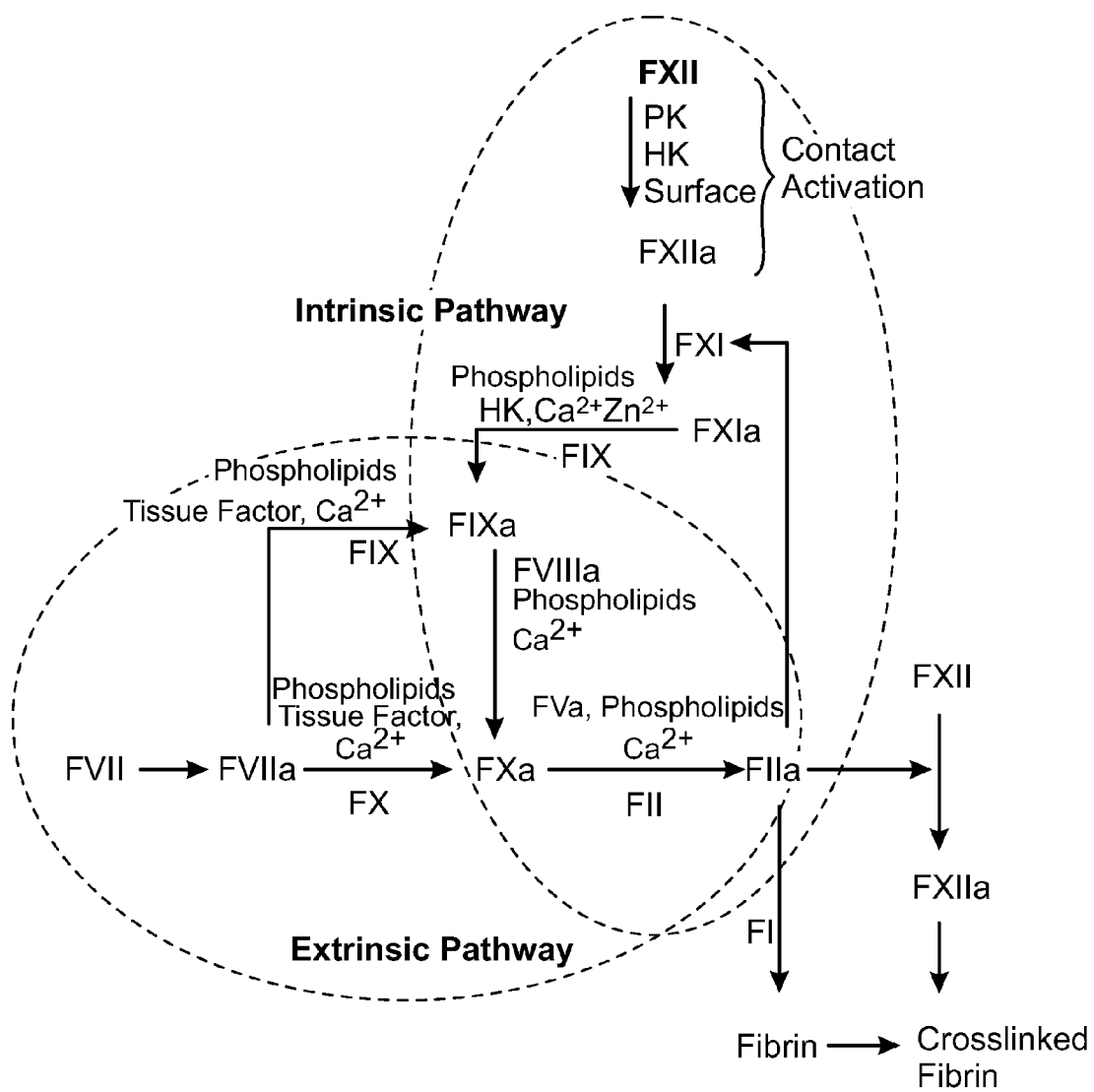
FIG. 1 is a summary of the coagulation cascade, as known in the prior art.
Figure 2:
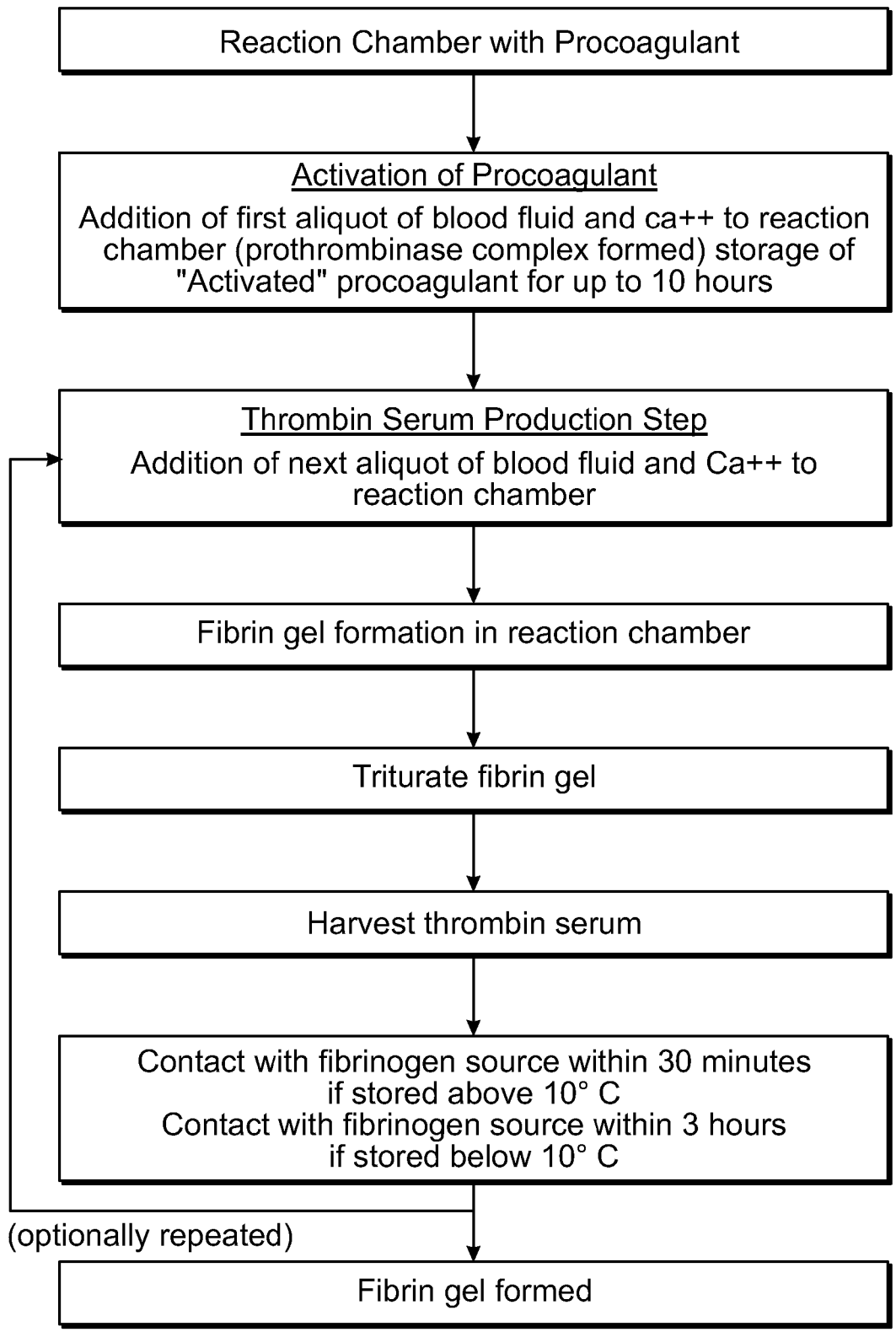
FIG. 2 is a flow diagram detailing the method in a preferred embodiment of the invention.

Beginning first at FIG. 2 the procedure of the current invention in the preferred embodiment comprises four steps, which preferably occur sequentially: 1) An activated procoagulant agent surface is prepared through combining and then incubating for about 10 minutes a first biologic fluid aliquot that is coagulation cascade competent in the presence of free calcium ions; 2) the activated procoagulant agent may then be stored for a period up to about 10 hours; 3) at about between 1 minute to 10 hours from the addition of the first blood fluid and at a time when it is anticipated thrombin will be needed (planned thrombin use), an additional aliquot of biologic fluid and free $Ca^{++}$ ions is added to the activated procoagulant agent; and 4) the fibrin gel that subsequently forms is triturated to release thrombin serum which can then be harvested. The thrombin can be applied to a fibrinogen source to generate fibrin. The thrombin can be applied topically as a liquid alone, sprayed into a mist or used with another carrier such as absorbable hemostatic agents including gelatin sponge, oxidized regenerated cellulose, and microfibrillar collagen or combined with fibrinogen to create a "glue" or "gel".

For purposes of this application, it should be noted that "activated" procoagulant agent and procoagulant agent are not one in the same. An activated procoagulant agent will cause plasma gelling at a much faster rate than a procoagulant agent that has not been activated. In on identification scheme, an activated procoagulant agent can be identified by comparing from two samples the time it takes each procoagulant agent sample to cause gelling in fresh frozen plasma containing citrate as the anticoagulant wherein the plasma has been thawed within two hours of its intended use. Specifically, in a first 12 mm×75 mm polystyrene test tube, 0.5 grams of a procoagulant agent that has previously been contacted with blood fluid is added. In a second similar test tube the same procoagulant agent that has not had prior contact with blood fluid is added as a control. To each tube 2 ml of thawed fresh frozen plasma containing citrate as the anticoagulant is added wherein the plasma has been thawed within 2 hours of its intended use and record the time of addition as time zero. The length of time it takes for the liquid plasma in each tube to be converted to a gel is recorded, and if the elapsed time for the test procoagulant to cause plasma gelling is twice as fast or greater than the time for control procoagulant to cause plasma gelling, then the test procoagulant is determined to be activated procoagulant agent. If the elapsed time for the test procoagulant to cause plasma gelling is less than twice as fast than the time for control procoagulant to cause plasma gelling, then the test procoagulant is determined not to be activated procoagulant agent.

Returning to the present invention in its preferred embodiment, it is also noted that harvested thrombin is transiently stable and may be added to a fibrinogen source to form fibrin within 30-minute period stored at room temperature. If rapid formation of fibrin is desired (fast clot time), it is preferable to contact the fibrinogen with the harvested thrombin within a 15-minute period and even more preferably immediately (within 5 minutes) after harvesting the thrombin. If the planned thrombin use is delayed, the thrombin can be stored on ice (<10° C.), which will significantly enhance the stability of the thrombin so that it may be used within 3 hours and more preferably within 60 minutes.

Figure 6:
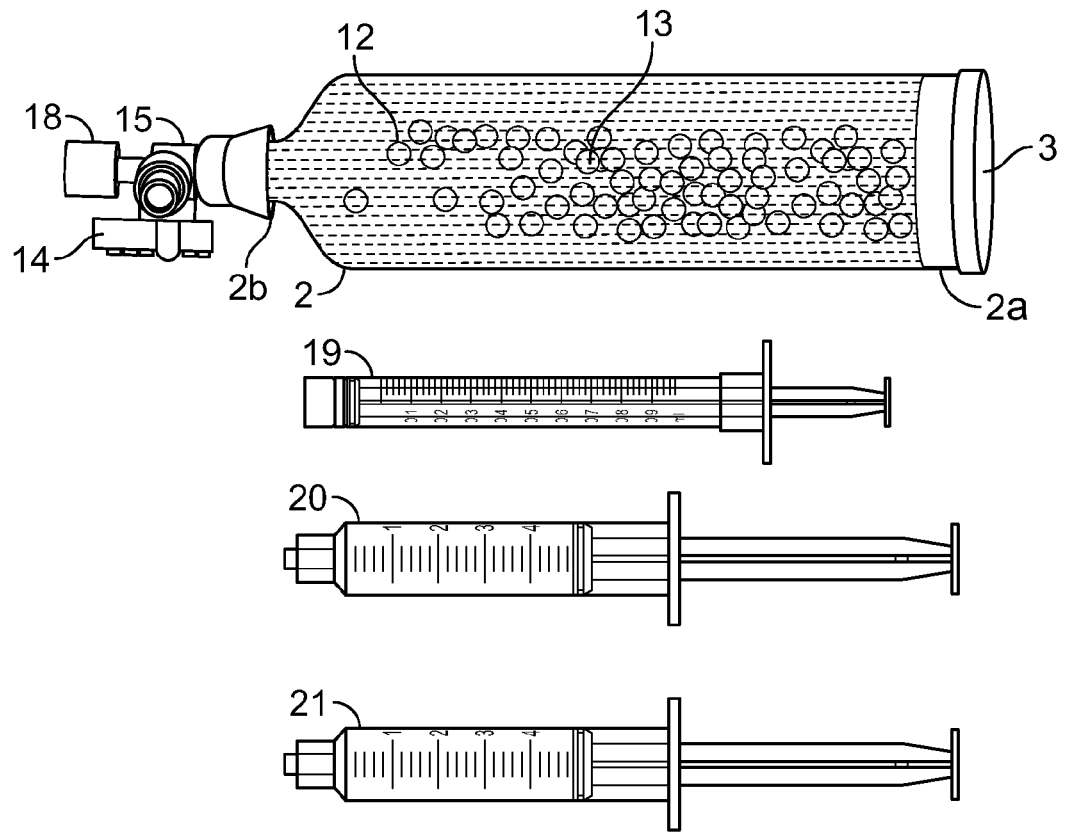
FIG. 6 is a drawing of an exemplary reaction chamber along with syringes for use in conjunction with the exemplary reaction chamber for harvesting thrombin serum.
Figure 6A:
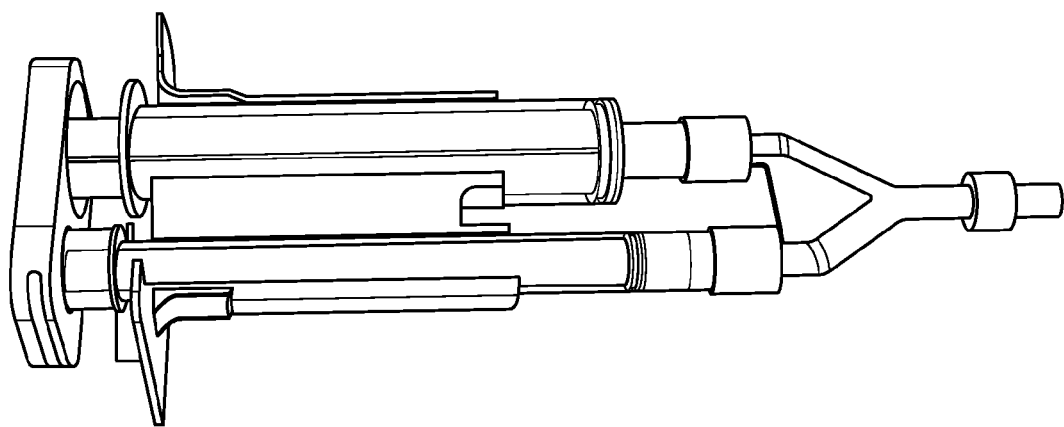
FIG. 6A is a prior art drawing of a spray tip applicator used for delivery of harvested thrombin to form fibrin at a point of need.

Expressing the thrombin solution through a filter containing a porous membrane (e.g., 20 to 80 micron pore size) will retain procoagulant agent and remove fibrin particulate matter, which otherwise could prevent the thrombin from spraying through a small orifice or expressing the thrombin through a thin tube onto a wound site using a device as shown in FIG. 6A. FIG. 6A is a prior art drawing of a spray tip applicator in which one syringe is filled with a fibrinogen source and the second syringe is filled with thrombin serum, and wherein the contents of the two syringes are mixed as they are ejected through an atomizer element to create an aerosol spray which will deliver the mixture as a liquid that will quickly become a solid due to the formation of fibrin and act as a sealant.

Figure 4A:
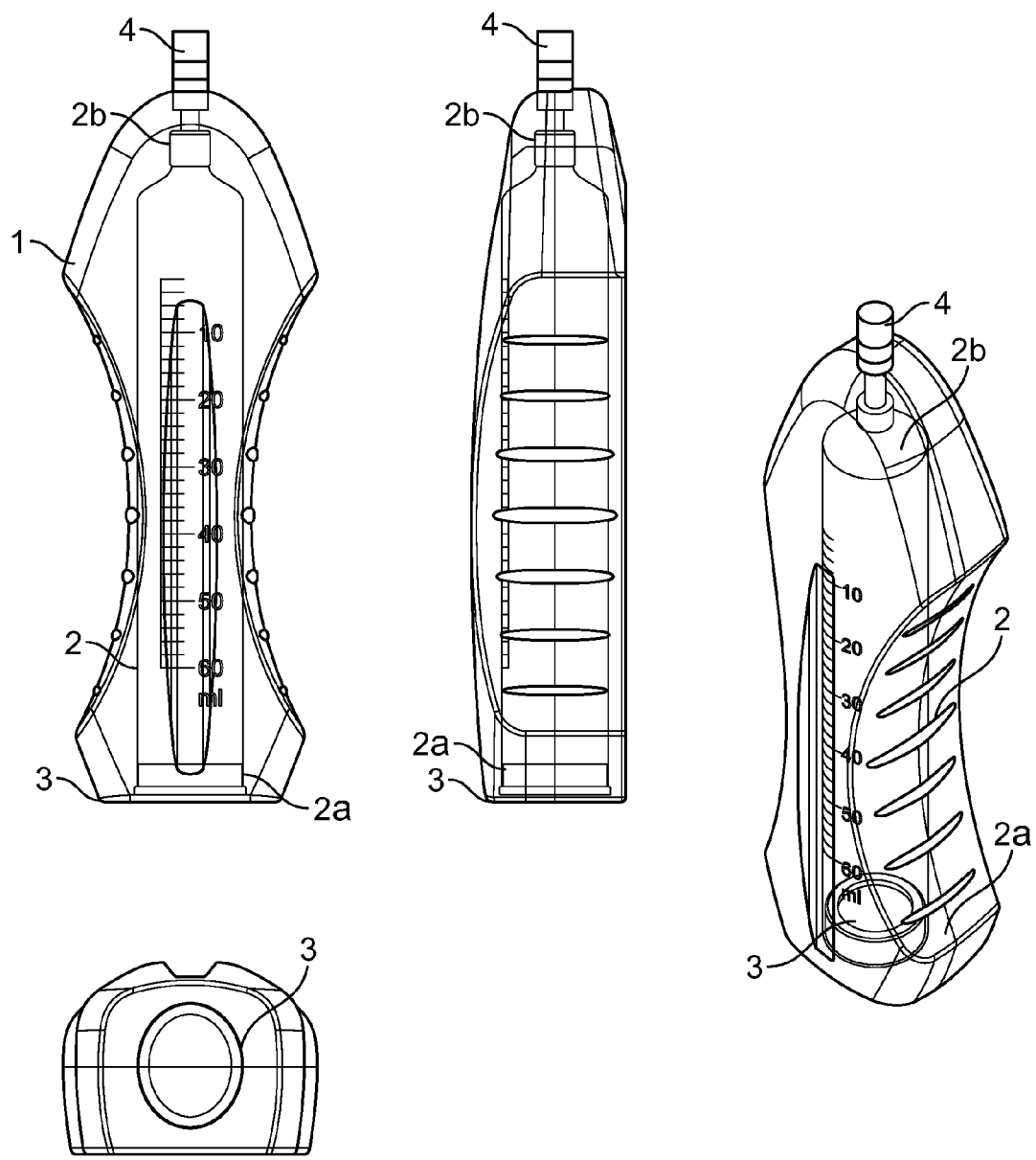
FIG. 4a is one embodiment of a reaction chamber cover according to an embodiment of the invention.
Figure 4B:
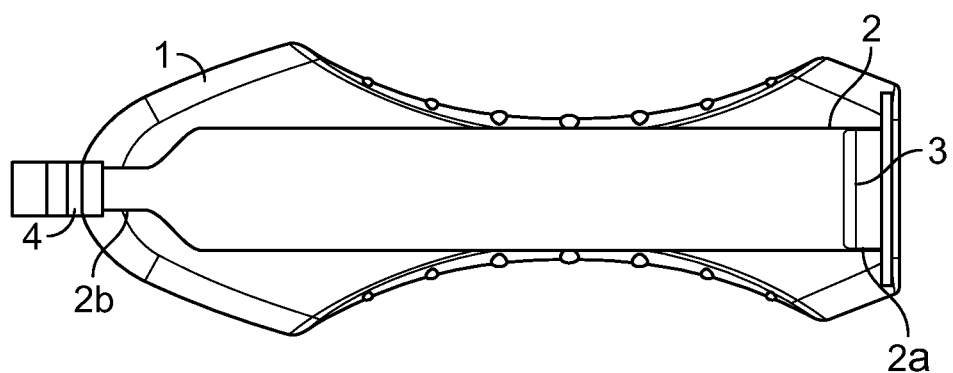
FIG. 4b is a top plan view of a reaction chamber cover and reaction chamber according to an embodiment of the invention.
Figure 4C:
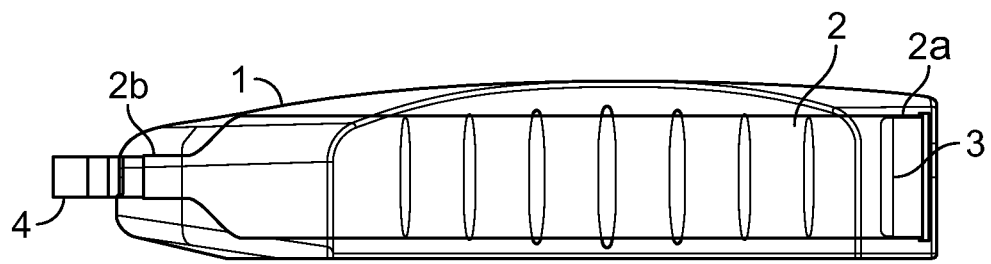
FIG. 4c is a side view of the reaction chamber cover and reaction chamber according to an embodiment of the invention.
Figure 4D:
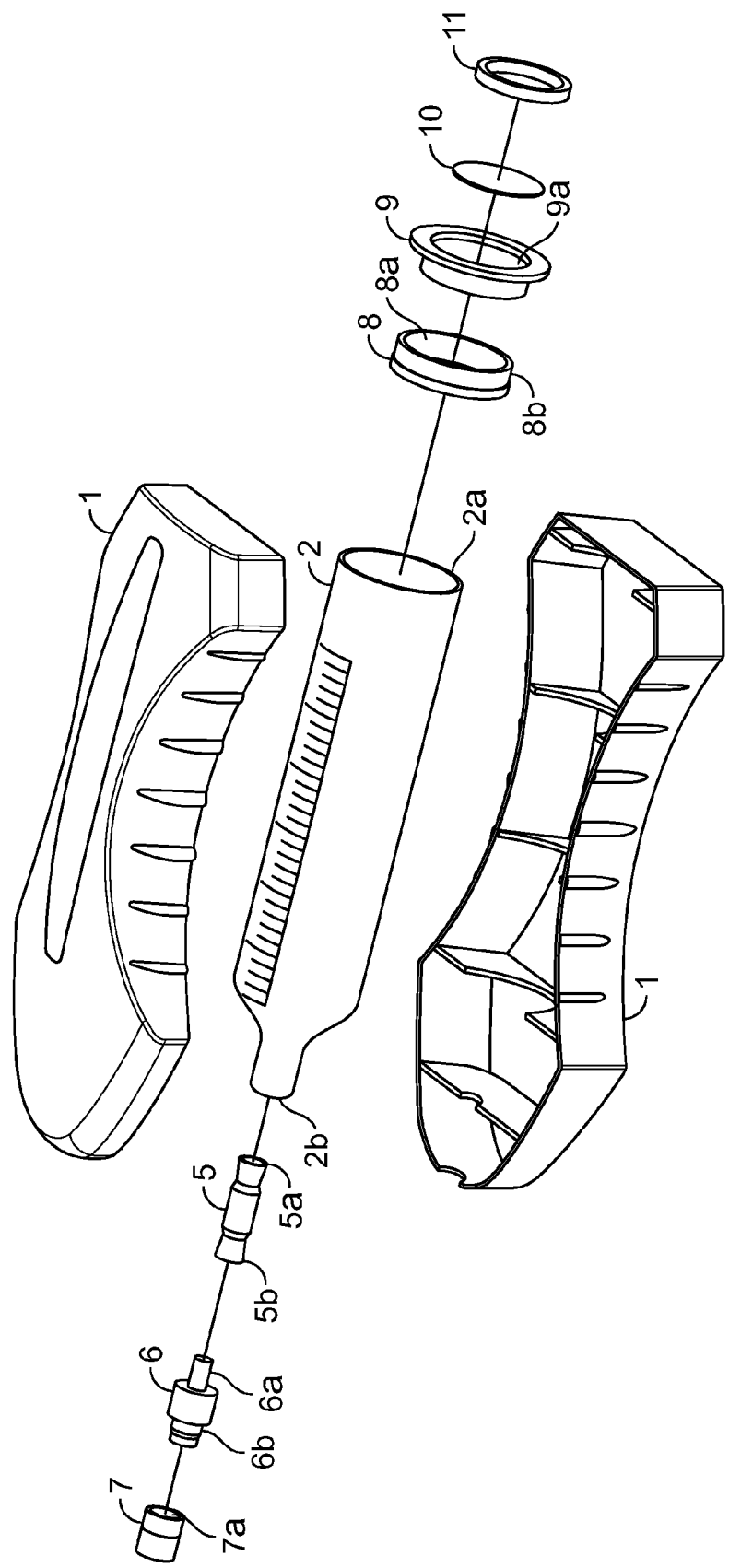
FIG. 4d is an exploded perspective view of the reaction chamber cover and reaction chamber according to an embodiment of the invention.

Turning now to FIG. 4A-FIG. 4D, one aspect of the invention is shown. FIG. 4A-FIG. 4C shows various view of the apparatus used to practice the method. The apparatus includes a casing 1 enclosing a reaction chamber 2. The reaction chamber 2 is preferably a cylindrical chamber having a broad end 2a and a narrow end 2b. The broad end 2a has a cap structure 3 that is configured to press fit into the opening at the broad end 2a. The narrow end 2b is configured to receive an adapter 4. Referring now to FIG. 4D, the figure shows an exploded view of the cap structure 3 and the adapter 4, according to an embodiment of the invention. The narrow end 2b is configured to form a nozzle-like structure 2c, the nozzle like structure 2c connected to the adapter 4 (see FIG. 4A to FIG. 4C). The adapter 4 comprises a double luer female adapter 5. The double luer female adapter 5 has a first end 5a and a second end 5b. 5a is adapted to fit into the nozzle-like structure 2c. 5b is adapted to receive a first end 6a of a needleless access port 6. The second end 6b of the needless access port 6 is configured to form a threaded structure 6b. The threaded structure 6b of the needleless access port 6 is connected to a cap 7. The cap 7 prevents contamination of the needleless access port 6. The cap structure 3 includes a seal 8. The seal 8 is an annular structure, the inner ring 8a configured for being received by a cap 9 and the outer ring 8b configured for a snug fit into the broad end 2a of the container 2. The cap 9 has a depression 9a configured for receiving and retaining a filter membrane 10. The filter membrane 10 is retained in the depression 9a of the cap 9 through a retainer 11.

The apparatus as described herein comprises a sterile, non-pyrogenic fluid path container having a means to introduce, contain and remove a fluid without leaking and preferably without the fluid being in direct contact with open room air so as to reduce the risk of microbial contamination, the container also acting as a reaction chamber for the activation of the coagulation cascade, the reaction chamber containing a procoagulant agent in sufficient amount and surface area to efficiently activate the coagulation cascade in the volume of biologic fluid intended to be employed, the reaction chamber further having a shape that enables intimate contact of the procoagulant agent with the biologic fluid during each incubation step, and containing a means to triturate fibrin gels formed therein preferably by containing relatively larger detached objects with greater mass than the procoagulant agent and the reaction vessel is designed to have sufficient internal surface area within the chamber such that mechanical agitation of the reaction chamber (e.g., shaking) by the operator causes the larger detached objects to move and break up the fibrin gel surrounding the smaller procoagulant agent. A ratio of volume of at least two times the combined volume of the biological fluid, procoagulant agent and detached large objects is preferred. Upon trituration of the gel, the movement of the large detached objects within the reaction chamber creates an audible sound alerting the operator that the trituration has been accomplished. The larger detached objects are made of medical grade plastic spheres or glass spheres. A preferable shape and diameter of such large detached objects are spheres having a 5 to 15 mm diameter composed of medical grade plastic or glass. The reaction chamber preferably provides a means for the introduction of calcium ions in solution preferably in an amount of solution that is less than 10% of the volume of the intended blood fluid aliquot and further where the calcium ions are derived from calcium chloride. The amount of calcium ions required to be added can be readily determined by experimentation by one skilled in the art but should be sufficient to recalcify the blood aliquot which generally occurs wherein the final concentration of calcium chloride added is 5 to 30 mM and more preferably 10 to 20 mM. Calcium may be added anywhere on the fluid path after the swabbable valve because the plasma injected to the system will carry it to the reaction chamber. As one less preferred but useful example described in more detail below provides that dry calcium may be placed between the stopcock and one-way duck bill valve.

The following is a detailed description of an exemplary method for preparing thrombin serum from human plasma according to a preferred embodiment of the invention.

Figure 5:
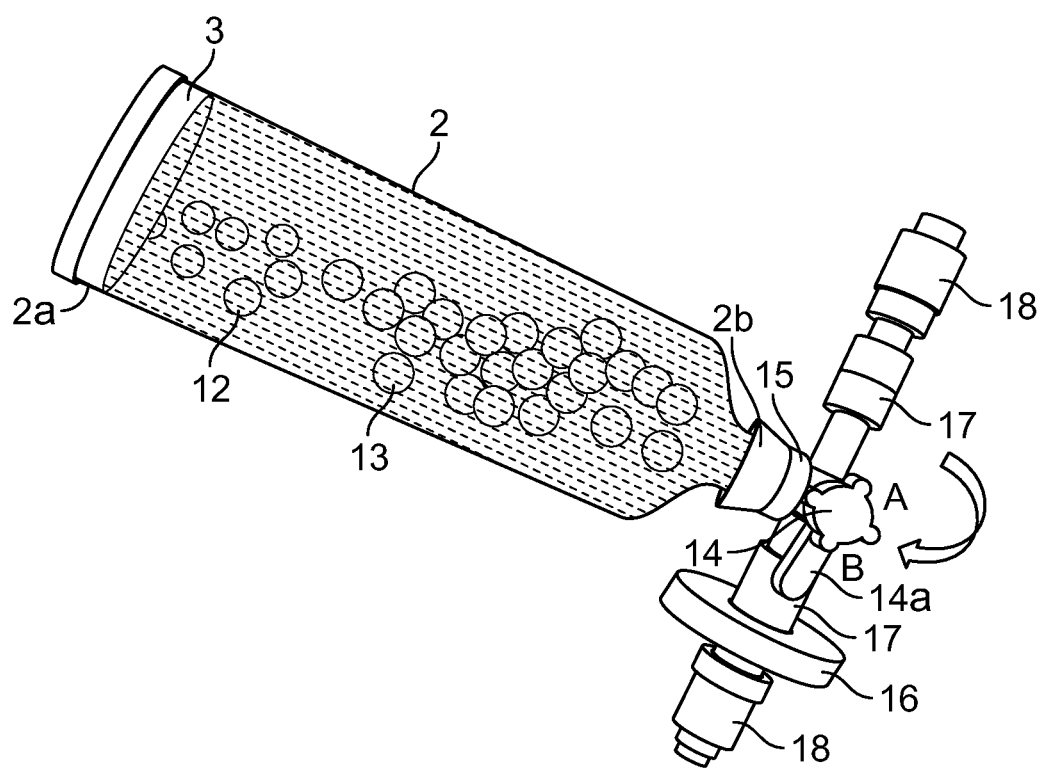
FIG. 5 is a drawing of an exemplary assembled reaction chamber along with an arrangement for harvesting thrombin serum.

A drawing of an exemplary apparatus used to practice the method is shown as FIG. 5. In this exemplary embodiment, the apparatus includes a reaction chamber 2 having a procoagulant agent 12. The reaction chamber 2 also has detached spheres 13 for triturating the fibrin gel. A four-way stopcock 14 comprising a flow control handle 14a is provided for controlling the flow of fluids from and into the reaction chamber 2. A one-way duckbill valve 15 is connected to the reaction chamber 2 and prevents fluid from egressing out of the reaction chamber 2. A filter housing 16 containing a membrane with a pore size of about 20 microns is connected at one of the ends of the four-way stopcock 14 for retaining particulate matter including procoagulant agent and fibrin particles. The apparatus further comprises a swabbable one-way needle-less access port 17 to improve the microbial safety of the apparatus by avoiding open air contact during transfer of fluids into and out of the reaction chamber 2.

Preparation of Reaction Chamber.

Although various suitable vessels may be employed, in this exemplary embodiment a 60 ml syringe provides a convenient prototype reaction chamber 2. The reaction chamber 2 may be prepared by removing the syringe plunger and adding glass spheres as procoagulant 12. In this exemplary method, and by way of one example, 20 grams of glass beads having a diameter between 0.5 and 5 mm may be used as procoagulant agent 12. In addition, 7 grams of large polystyrene beads (10 mm diameter) or other suitable materials may be added to the reaction chamber as solid detached objects 13 for triturating formed fibrin gels. The plunger may then be returned to the 50 mL mark on the syringe to create sufficient space for the large detached beads 13 to move during shaking so as to break up (triturate) the formed fibrin gel. The plunger is not required to move and may remain in a fixed position for the duration of the thrombin serum production. Commercial embodiments of the present invention may alternatively use an injection-molded vessel instead of a syringe as the reaction vessel. The 4-way stopcock 14 with hand lever 14a is included in a preferred embodiment so as to provide means of directional control of fluid movement into and out of the reaction chamber. The stopcock 14 is turned to a first position A where the fluid path is from the first needleless access port 17, through the one way duckbill valve 15 and then into reaction chamber 2 (syringe barrel in present example). FIG. 6 is a drawing of an exemplary reaction chamber along with syringes for use in conjunction with the exemplary reaction chamber for harvesting thrombin serum. The exemplary reaction chamber as described herein is used in conjunction with other syringes 19, 20 and 21 for delivering fluids such as biological fluid and calcium ion containing fluid. The fluids may be injected into the device when the stopcock is in position A. The stopcock handle 14a may be turned to a second position B where the fluid path is from the second needless access port 18, through the filter 16 and then into the reaction chamber 2 (syringe barrel in present example). In this stopcock handle position B, a syringe may be attached to the second swabbable access port and the syringe plunger may be withdrawn so as to create a low pressure volume or vacuum that result in thrombin serum being drawn out of the reaction chamber 2 through the filter 16 and into the syringe. In the preferred embodiment of the present invention, the filter having a porous membrane, with a pore mesh size sufficiently small that it retains the procoagulant agent (too small to be shown in this Figure) and fibrin particulate but enables flow of thrombin serum to occur, is included. The microbial safety of the apparatus can be enhanced by providing a closed system that is achieved by including leak-free aseptic swabbable access ports for syringes to access the apparatus.

Preparation of CaCl$_2$ Solution.

A 354 mM calcium chloride hexahydrate (Sigma, St. Louis, Mo., Product No. 21110-1KG-F, Lot #BCBC3343, MW 219.08) solution may be prepared by dissolving 15.5 grams in 200 ml of water. For each 5 ml of citrate anti-coagulated blood fluid, 0.2 ml of CaCl$_2$ solution may be added to recalcify the blood fluid solution with a final concentration of about 14 mM. A 1 mL syringe may be used to deliver the CaCl$_2$ into the reaction chamber via the swabbable port. Alternatively, dry calcium may be present in the chamber before the procedure starts and the presence of dry calcium obviates the need for liquid calcium to be used at later steps in the method.

Blood Fluid.

By means of non-limiting example, citrate anti-coagulated whole blood or citrated anti-coagulated human fresh plasma may be used as convenient blood fluids for experimental purposes.

Spray Application of Thrombin Serum.

Upon harvesting the thrombin serum, a spray tip applicator such as that manufactured by Micromedics Corp., St. Paul, Minn. (see Fibrijet Blending connector with spray tip SA-3674 as shown in prior at FIG. 6A) may be used to apply the thrombin serum in combination with another aliquot of the thawed plasma as the source of fibrinogen.

One embodiment of a preferred procedure for the production of thrombin serum according to the present invention is detailed below:

Step 1: a reaction chamber prepared as described above is loaded with first incubation reactants:
  a. A 1 ml syringe containing CaCl$_2$ solution is attached to the reaction chamber via the needle-less access port and 0.2 mL is injected, then the syringe is detached.
  b. A 5 ml syringe containing 5 ml of plasma is attached to the reaction chamber via the needless access port and all the plasma is injected into the reaction chamber and then the syringe is detached.
  c. With the reaction chamber held in the horizontal position, the contents are mixed to completely wet the procoagulant agent by gently shaking the reaction chamber sufficiently to cause the movement of procoagulant agent and the detached large plastic beads.

Step 2. First Incubation
  a. The syringe is laid on a flat level surface with procoagulant agent distributed evenly and the first incubation cycle begins, which can be from about 10 minutes to about 10 hours.
  b. After about 10 minutes, sufficient thrombin is generated to convert the soluble fibrinogen in the biologic fluid to become insoluble fibrin leading to a first fibrin gel being formed. The fibrin gel is readily apparent by visual inspection due to the loss of fluidity of the mixture and by observation the procoagulant and plastic beads becoming caked to the reaction wall even when the reaction chamber is held in a vertical position.

Step 3. When thrombin serum is needed for use, the reaction chamber is loaded with the second incubation reactants.
  a. 1 ml syringe containing CaCl$_2$ solution is attached to the reaction chamber via the needless access port and 0.2 mL is injected before the syringe is detached.
  b. A 5 ml syringe containing 5 ml of plasma is injected to the reaction chamber via the needless access port.
  c. With the reaction chamber held in the vertical position, the first formed fibrin gel is triturated and the chamber contents are mixed by firmly shaking the reaction chamber up and down until all the beads are moving freely within the reaction chamber (approximately 3 to 10 seconds).

Step 4. Second Incubation
  a. The syringe is laid on a flat level surface with glass beads distributed evenly and the second incubation cycle begins, which can be from about 1 minute to about 60 minutes. The thrombin serum is ready to be harvested as soon as the second fibrin gel is formed. The fibrin gel is evident because the plasma is no longer in a liquid state and the bead contents are stably plastered to the reaction vessel wall. This method produces a thrombin preparation that is transiently stable and the thrombin clotting activity of fibrinogen decreases with storage time in the fibrin gel. Therefore, for greatest thrombin reactivity to be present in the thrombin serum, it is preferable to triturate the fibrin gel and harvest the thrombin serum as described below as soon as the fibrin gel is formed (e.g., about or less than 15 minutes after addition of second fibrin gel is formed, more preferably about or less than 5 minutes after second fibrin gel is formed and most preferably about or less than 1 minute after second fibrin gel is formed).

Figure 7:
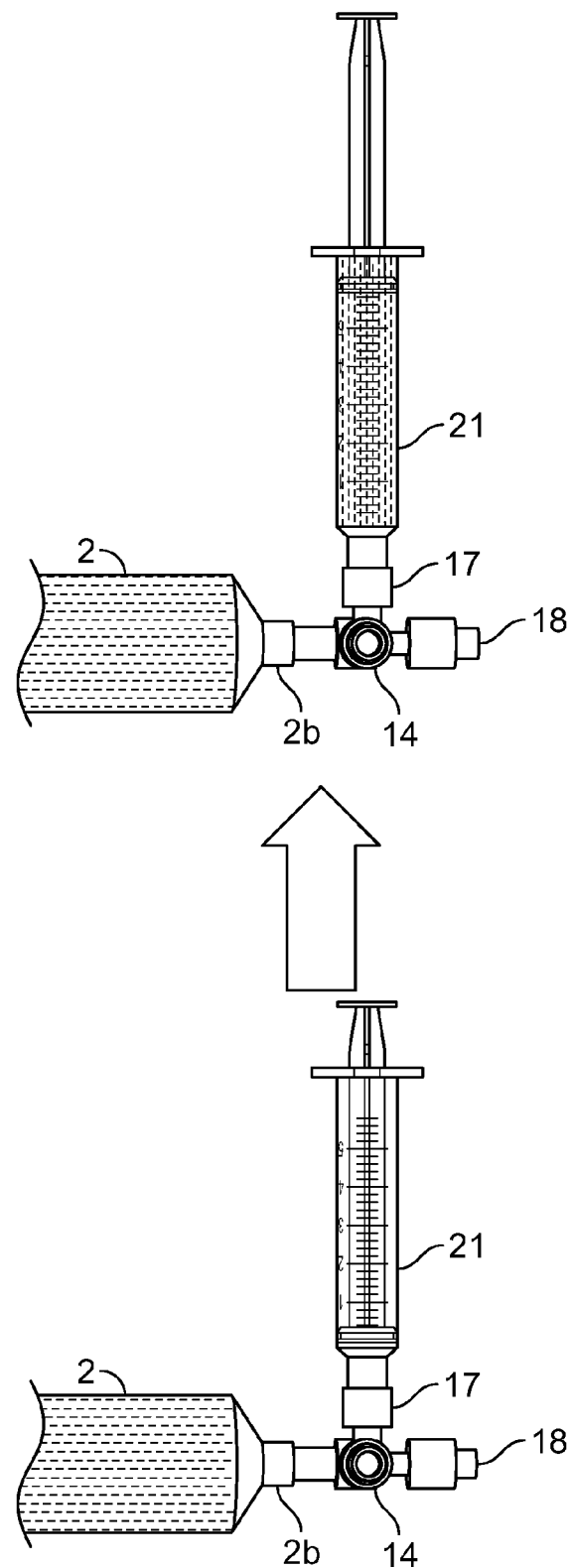
FIG. 7 is a drawing illustrating the harvesting of thrombin serum from an exemplary reaction chamber according to an embodiment of the invention.
Figure 8:
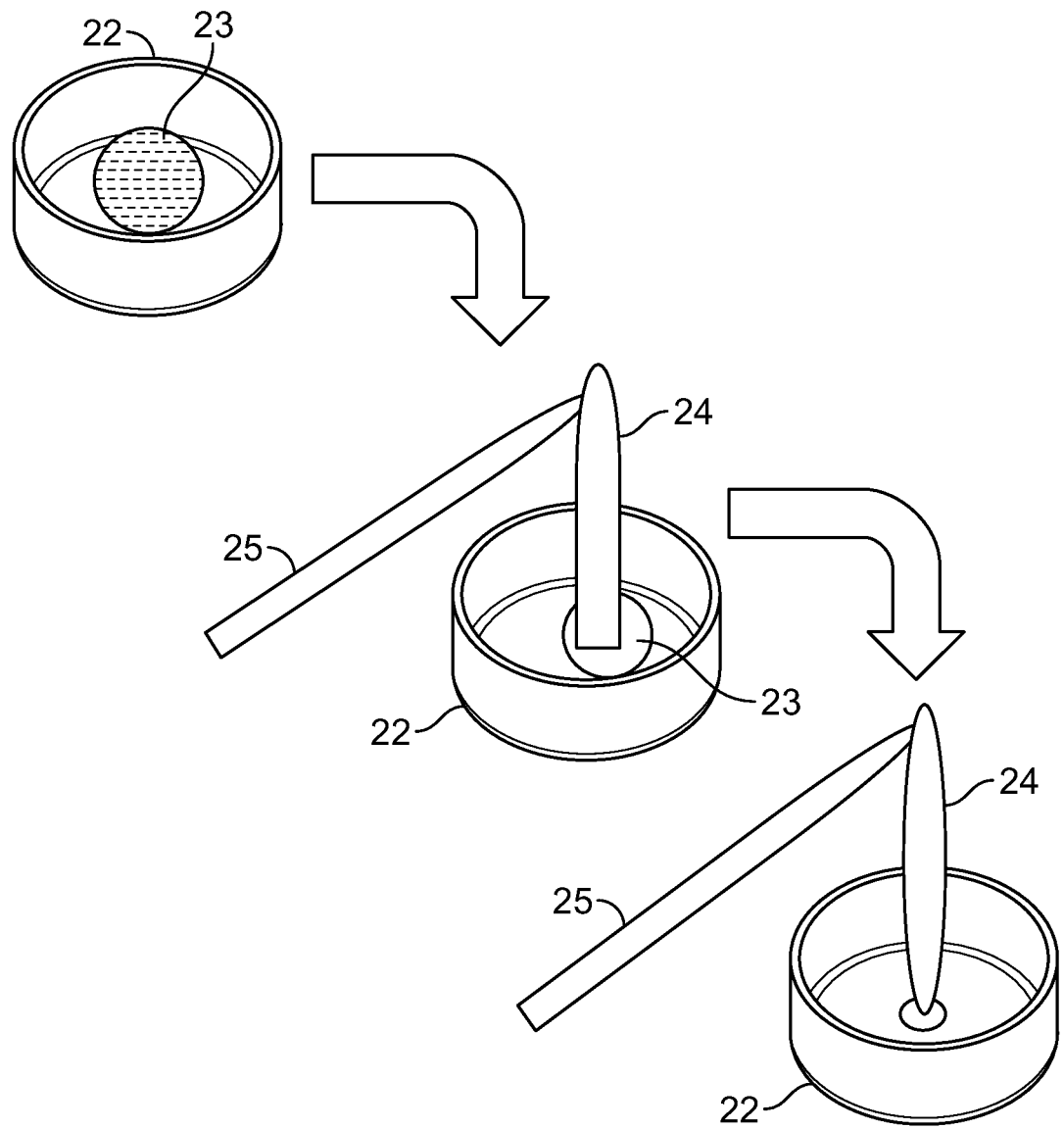
FIG. 8 shows the formed fibrin gel is strong enough to support its own weight.

Step 5. Thrombin Serum Harvest using 10 ml syringe
  a. After second fibrin gel is formed, the reaction chamber is agitated with sufficient force to dislodge the beads in the chamber so as to break up the fibrin gel present.
  b. A filter with porous membrane is attached to the swabbable port attached to the reaction chamber so as prevent the passage of particulate matter into a 10 ml harvest syringe.
  c. The reaction chamber is placed in a vertical position so that the 10 ml syringe is below the reaction chamber and the thrombin serum is harvested by pulling back on the plunger of the 10 ml syringe to create a low pressure region or vacuum within the reaction chamber until the desired amount of thrombin serum (up to about 5 ml) is harvested as shown in FIG. 7, which is an illustration shows the harvesting of thrombin serum from an exemplary reaction chamber 2 achieved through pulling back on a syringe plunger 21 to create a vacuum and then waiting until the desired amount of thrombin serum vacates the reaction chamber to enter the syringe 21.
  d. The harvested plasma can be stored at room temperature and used to contact fibrinogen to form fibrin within 15 minutes of addition of second blood fluid aliquot or it can be stored on wet ice (<10° C.) and used to contact fibrinogen to form fibrin within 1 hour of addition of second blood fluid aliquot.

Step 6. (Optional) If it is desired to make additional thrombin serum preparations, steps 3, 4, and 5 may be repeated using fresh aliquots of blood fluid up to at least six times.

The discovery that prothrombinase enzyme complex once formed on the procoagulant agent surface during the initial contact of mixing blood fluid, calcium and the procoagulant agent in the apparatus remains in a persistent functional state of sustained enzymatic activity to be able to rapidly convert prothrombin to thrombin for a clinically useful period of time of at least ten hours but less than twenty-four hours was illustrated in the experiment summarized below.

In this study six reaction chambers were prepared as described above. The representative blood fluid employed for this experiment was fresh plasma. Addition of plasma and calcium to the reaction chamber (Steps 1) was performed as described above for all six syringes at a time designated as Time Zero. The duration of the first incubation period (Step 2) was varied for each of the six syringes to have incubation test conditions of 0 hour, 1 hour, 3 hours, 10 hours, 12 hours, and 24 hours. The addition of the second calcium and plasma aliquots to the reaction chamber (Step 3) was performed at the end of the first incubation time as described above. The second incubation (Step 4) was fixed to the time required for the second gel to form, which was recorded. The harvest of the thrombin serum was performed as described above (Step 5) and the thrombin activity measured after 5 minutes after thrombin serum harvest. The thrombin activity in this experiment was measured by recording fibrinogen clot times using a STart Hemostasis Analyzer manufactured by Diagnostica Stago Inc., Troy Hills, N.J. The data presented in the table below demonstrates that a storage time of 12 hours or more results in loss of procoagulant activation as the time for the fibrinogen clotting began to increase due to less thrombin activity, however even at 12 hours it was not completely lost as was the case after 24 hours of storage. Interestingly, each batch of thrombin prepared extended the procoagulant activity for an additional 10 hours or more. The data in the table below demonstrates the stability of activated procoagulant agent for at least 10 hours of storage time at room temperature.

TABLE A

Effect of storage time on persistence of activation of the procoagulant agent

| Reaction Chamber Apparatus # | Time Elapsed between First and Second Incubation Times (hours) (Steps 2 and 3) | Time Required for Second Gel to Form After addition of Second Aliquots of Plasma and Calcium (Step 4) | Harvested Thrombin serum activity (Clot time measured in seconds) | Status of the Procoagulant Agent |
|---|---|---|---|---|
| 1 | 0 | <1 minute | <10 seconds | Activated |
| 2 | 1 | <1 minute | <10 seconds | Activated |
| 3 | 3 | <1 minute | <10 seconds | Activated |
| 4 | 10 | <2 minute | <10 seconds | Activated |
| 5 | 12 | <3 minutes | <20 seconds | Activated |
| 6 | 24 | >5 minutes | >120 seconds | Non-activated |

An experiment demonstrating the proof of concept that multiple preparations of thrombin serum can be derived from a single apparatus was conducted according to the method taught above. Here, thrombin serum preparations were prepared from thawed fresh frozen plasma five times at 30-minute intervals using a single apparatus. The data in the table below demonstrates that a single apparatus can be used repetitively to produce thrombin with high reactivity on demand. The procoagulant agent was activated by adding 0.2 mL of $CaCl_2$ solution and 5 ml of freshly thawed plasma to the reaction chamber and incubated until first gelling occurred, which required approximately 5 minutes. At this point, the procoagulant surface is activated and can produce thrombin serum on demand. To generate thrombin serum, an additional 0.2 mL of $CaCl_2$ solution and 5 ml of plasma was added to the reaction chamber and incubated until second gelling occurred, which required approximately 30 seconds. After about a 1-minute hold after the gel was formed, the apparatus was agitated to break the gel and about 5 ml of thrombin serum harvested. The thrombin reactivity in the sequestered serum was determined by performing a clot test. In an exemplary clot test, 0.5 ml of a thrombin serum is added to 0.5 ml of fibrinogen source such as plasma in a 1.5 mL Eppendorf tube. The sample is mixed by inversion and time required for the liquid solution to become a solid or gel is determined by observation. The data demonstrates that a single apparatus could produce at least 4 batches of 5 ml thrombin serum/batch.

TABLE B

Demonstration of single apparatus preparation of multiple batches of thrombin serum

| Blood Aliquot Contacting Procoagulant Agent | Time Elapsed since First Blood Aliquot Addition to Procoagulant Agent and Next Blood Aliquot Added | Observed Incubation Time with Procoagulant Agent Required to Form Fibrin Gel in Reaction Chamber | Time Elapsed Between Addition of Blood Aliquot and Clot Test | Observed Clot Time |
|---|---|---|---|---|
| 1st | Not Applicable (NA) | 5 minutes | No harvest of thrombin serum | NA |
| 2nd | 30 min | ~30 seconds | 1 min | <15 sec |
| 3rd | 60 min | ~30 seconds | 1 min | <15 sec |
| 4th | 90 min | ~30 seconds | 1 min | <15 sec |
| 5th | 120 min | ~30 seconds | 1 min | <15 sec |

An experiment was also conducted to measure the stability of thrombin serum prepared with teachings of the present invention. Here, thrombin serum preparations were prepared from thawed fresh frozen plasma using a single apparatus. The procoagulant agent was activated by adding 0.2 mL of $CaCl_2$ solution and 5 ml of freshly thawed plasma to the reaction chamber and incubated until first gelling occurred, which required approximately 5 minutes. To generate thrombin serum, an additional 0.2 mL of $CaCl_2$ solution and 5 ml of plasma was added to the reaction chamber and incubated until second gelling occurred, which required approximately 30 seconds. After about a 1-minute hold after the gel was formed, the apparatus was agitated to break the gel and about 5 ml of thrombin serum harvested. The thrombin serum preparations were then stored at room temperature or at <10° C. and the thrombin reactivity measured periodically thereafter. The thrombin reactivity in the sequestered serum was determined by performing a clot test. The clot time for the thrombin serum was measured over a 30 min period to detect its stability both at room temperature and when stored at <10° C. The clot time gradually increased over a 3-hour period. The fastest clotting time (e.g., greatest thrombin concentration) was achieved immediately after harvesting the thrombin serum. Fast clotting activity remained for first 15 minutes after preparation and persisted for more than 30 minutes with clot times being less than 90 seconds. When the thrombin serum was stored in the cold, the rapid clotting activity was well maintained over a 60-minute period and persisted for up to at least three hours.

Returning briefly to the alternative embodiment wherein dry calcium chloride (as opposed to liquid calcium) is employed, in yet another embodiment this dry calcium chloride could be introduced to the reaction chamber at the time of manufacture of the apparatus. With the calcium present, it would necessarily contact each blood fluid aliquot introduced. This embodiment provides a benefit in that the number of steps required by the operator is reduced, consequently reducing the risk of error.

As one exemplary case of this dry calcium alternative embodiment, one experiment utilized thrombin serum preparations prepared from thawed fresh frozen plasma using a single apparatus. The apparatus was prepared by adding 0.4 ml of $CaCl_2$ solution (354 mM calcium chloride hexahydrate prepared by dissolving 15.5 grams in 200 ml of absolute ethanol) to the reaction chamber containing procoagulant agent. The ethanol was allowed to evaporate leaving a dry calcium salt in the reaction chamber. Thrombin serum was prepared with this apparatus containing dry calcium salt by activating the procoagulant reagent with 5 ml of citrate anti-coagulated plasma without the addition of liquid calcium chloride solution. The activated procoagulant was next used to prepared thrombin serum by adding an additional 5 ml of citrate anti-coagulated plasma. It was surprising to learn that the initial concentration of calcium present in the first aliquot of plasma which is twice that normally used did not inhibit the successful formation of the procoagulant agent. Such inhibition in formation of activated procoagulant agent was observed when the amount of calcium dried in the reaction chamber was increased to 0.8 ml of $CaCl_2$ solution (354 mM calcium chloride).

Figure 3:
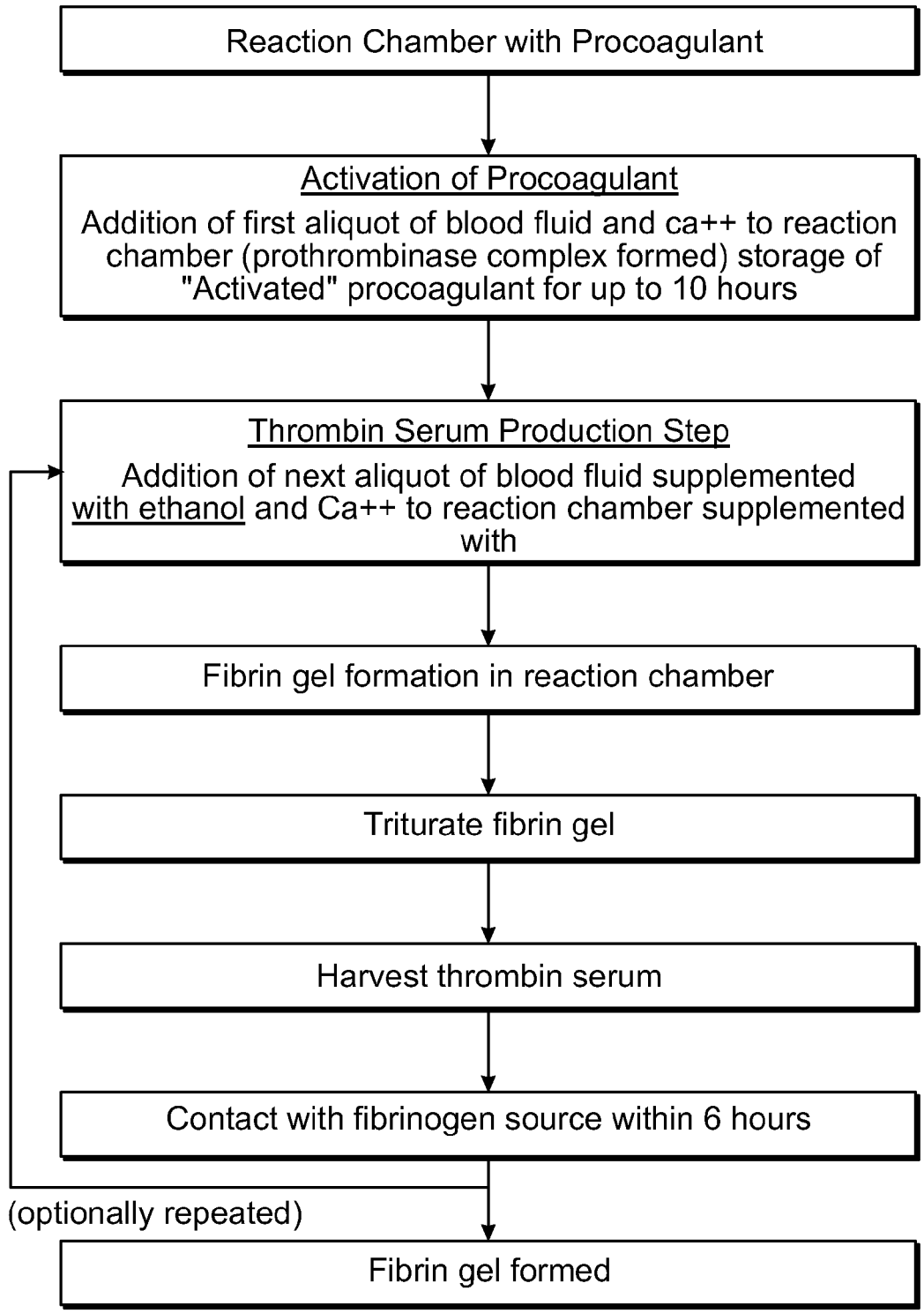
FIG. 3 is a flow diagram detailing the method in the preferred embodiment of the invention.

Although generally less desirable for many applications, it is possible to combine the teachings of the prior art of using ethanol to stabilize thrombin with the current invention of two stage thrombin serum production. FIG. 3 shows the procedure of the current invention in such an embodiment, wherein the two-stage procedure comprises four steps, which preferably occur sequentially: 1) An activated procoagulant agent (prothrombinase enzyme complex on the surface of the material) is prepared by combining a first biologic fluid aliquot that is coagulation cascade competent in the presence of free calcium ions and then incubating the mixture for at least about 10 minutes; 2) the activated procoagulant agent may then be stored for a period up to about 10 hours; 3) at a time when it is planned to use thrombin, an additional aliquot of biologic fluid supplemented with 15 to 25% ethanol (v/v) and free $Ca^{++}$ ions may be added to the activated procoagulant agent; and 4) the fibrin gel that subsequently forms is triturated. The thrombin serum supplemented with ethanol may then be harvested. The harvested thrombin supplemented with ethanol has enhanced stability particularly when stored at <10° C. and may be used to contact fibrinogen to form fibrin within 10 hours of addition of second blood fluid aliquot. Less preferably, this occurs within 6 hours of addition of second blood fluid aliquot. The procedure for the production of thrombin serum according to this embodiment of the present invention is detailed below:

Step 1: a reaction chamber prepared as described above is loaded with first incubation reactants:
  a. A 1 ml syringe containing $CaCl_2$ solution is attached to the reaction chamber via the needle-less access port and 0.2 mL is injected, then the syringe is detached.
  b. A 5 ml syringe containing 5 ml of plasma is attached to the reaction chamber via the needless access port and all the plasma is injected into the reaction chamber and then the syringe is detached.
  c. With the reaction chamber held in the horizontal position, the contents are mixed to completely wet the procoagulant agent by gently shaking the reaction chamber sufficiently to cause the movement of procoagulant agent and the detached large plastic beads.

Step 2. First Incubation
  a. The syringe is laid on a flat level surface with procoagulant agent distributed evenly and the first incubation cycle begins, which can be from about 10 minutes to about 10 hours.
  b. After about 10 minutes, sufficient thrombin is generated to convert the soluble fibrinogen in the biologic fluid to become insoluble fibrin leading to a first fibrin gel being formed. The fibrin gel is readily apparent by visual inspection due to the loss of fluidity of the mixture and by observation the procoagulant and plastic beads becoming caked to the reaction wall even when the reaction chamber is held in a vertical position.

Step 3. When thrombin serum is needed for use, the reaction chamber is loaded with the second incubation reactants.
  a. 1 ml syringe containing $CaCl_2$ solution is attached to the reaction chamber via the needless access port and 0.2 mL is injected before the syringe is detached.
  b. A 5 ml syringe containing 4 mL of 72% ethanol in water (v/v) is attached to the reaction chamber via the needle-less access port and the syringe contents are injected into the reaction chamber.
  c. A 5 ml syringe containing 5 ml of plasma is attached to the reaction chamber via the needle-less access port and entire contents of the syringe is injected before the syringe is detached.
  d. With the reaction chamber held in the vertical position, the first formed fibrin gel is triturated and the chamber contents are mixed by firmly shaking the reaction chamber up and down until all the beads are moving freely within the reaction chamber (approximately 3 to 10 seconds) so as to achieve a final concentration of about 20% ethanol (v/v) in the fluid contents of the reaction chamber.

Step 4. Second Incubation a. The syringe is laid on a flat level surface with glass beads distributed evenly and the second incubation cycle begin, which can be from about 1 minute to about 6 hours. The thrombin serum is ready to be harvested as soon as a second fibrin gel is formed. The fibrin gel is evident because the plasma is no longer in a liquid state and the bead contents are stably plastered to the reaction vessel wall. This method produces a thrombin preparation that is transiently stable and the thrombin clotting activity of fibrinogen decreases with storage time in the fibrin gel. Therefore, for greatest thrombin reactivity to be present in the thrombin serum, it is preferable to triturate the fibrin gel and harvest the thrombin serum as described below as soon as the fibrin gel is formed (e.g., about or less than 15 minutes after addition of second fibrin gel is formed, more preferably about or less than 5 minutes after second fibrin gel is formed and most preferably about or less than 1 minute after second fibrin gel is formed).

Step 5. Thrombin Serum Harvest a. After the second fibrin gel forms, the reaction chamber is agitated with sufficient force to dislodge the beads in the chamber, breaking up the fibrin gel present.

b. A filter with porous membrane is attached to the swabbable port attached to the reaction chamber so as prevent the passage of particulate matter into a 10 ml harvest syringe.

c. The reaction chamber is placed in a vertical position so that the 10 ml syringe is below the reaction chamber and the thrombin serum is harvested by pulling back on the plunger of the 10 ml syringe to create a low pressure region or vacuum within the reaction chamber until the desired amount of thrombin serum (up to about 5 ml) is harvested as shown FIG. 7. FIG. 7 illustrates the harvesting of thrombin serum from an exemplary reaction chamber 2 achieved through pulling back on a syringe plunger 21 to create a vacuum and then waiting until the desired amount of thrombin serum vacates the reaction chamber to enter the syringe 21.

d. The harvested plasma can be stored at room temperature and used to contact fibrinogen to form fibrin within 4 hours of addition of second blood fluid aliquot or it can be stored on wet ice (<10° C.) and used to contact fibrinogen to form fibrin within 6 hours of addition of second blood fluid aliquot.

Step 6. (Optional) If it is desired to make additional thrombin serum preparations, steps 3, 4, and 5 may be repeated using fresh aliquots of blood fluid up to at least six times.

Although the invention has been shown and described with respect to certain embodiments, it is obvious that equivalent alterations and modifications will occur to others skilled in the art upon the reading and understanding of the specification. In particular, with regard to the various functions performed by the above-described components, the terms (including any reference to a "means") used to describe such components are intended to correspond, unless otherwise indicated, to any component which performs the specified function of the described component (e.g., that is functionally equivalent) even though not structurally equivalent to the disclosed component which performs the functions in the herein exemplary embodiments of the invention. In addition, while a particular feature of the invention may have been disclosed with respect to only one embodiment, such feature may be combined with one or more other features of other embodiments as may be desired or advantageous for any given or particular application.

I claim:

1. A method for preparing thrombin serum, the method comprising the steps of:
   obtaining an activated procoagulant agent; and
   subsequently contacting said activated procoagulant agent with a blood fluid aliquot to form a mixture comprising fibrin gel;
   triturating said fibrin gel; and
   after said triturating step, extracting said thrombin serum from said mixture; and
   contacting said extracted thrombin serum with fibrinogen to obtain fibrin.

2. A method for preparing thrombin serum, the method comprising the steps of:
   contacting a first blood fluid aliquot with a procoagulant agent to form an activated procoagulant agent;
   storing said activated procoagulant agent;
   subsequently contacting a second blood fluid aliquot with said stored activated procoagulant agent to form a mixture comprising fibrin gel;
   triturating said fibrin gel; and
   after said triturating step, extracting said thrombin serum from said mixture; and
   contacting said extracted thrombin serum with fibrinogen to obtain fibrin.

3. A method for preparing ethanol stabilized thrombin serum, the method comprising the steps of:
   contacting a first blood fluid aliquot with a procoagulant agent to form an activated procoagulant agent comprising a prothrombinase enzyme complex bound to the surface of the procoagulant agent;
   storing said activated procoagulant agent;
   subsequently contacting said stored activated procoagulant agent with a second aliquot of blood fluid wherein ethanol is present at a concentration between about 15% to 25% by volume to form a mixture comprising fibrin gel;
   triturating said fibrin gel;
   after said triturating step, extracting thrombin serum from said mixture; and
   contacting said extracted thrombin serum with fibrinogen to obtain fibrin.

4. A method for preparing ethanol stabilized thrombin serum, the method comprising the steps of:
   contacting a first blood fluid aliquot with a procoagulant agent to form an activated procoagulant agent comprising a prothrombinase enzyme complex on the surface of the procoagulant agent;
   storing said activated procoagulant agent;
   after said storing step, contacting the activated procoagulant with a second aliquot of blood fluid wherein ethanol is present at a concentration between about 15% to 25% by volume to obtain thrombin serum supplemented with ethanol and form a mixture comprising fibrin gel;
   triturating said fibrin gel;
   after said triturating step, extracting thrombin serum supplemented with ethanol from said mixture; and
   contacting extracted thrombin serum supplemented with ethanol with fibrinogen to obtain fibrin.

5. The method according to any of claim 1, 2, 3 or 4 further comprising the step of obtaining blood fluid from a single donor and wherein said blood fluid aliquots are extracted from said blood fluid.

6. The method according to claim 5 wherein the blood fluid obtained is an autologous blood fluid.

7. The method according to claim 5 wherein the blood fluid is selected from the group consisting of whole blood, citrate anti-coagulated whole blood or plasma, plasma including platelet rich plasma, buffy coat rich plasma, platelet poor plasma, whole bone marrow, citrate anti-coagulated bone marrow, whole cord blood, citrate anti-coagulated bone marrow, blood fraction matter comprising prothrombin, and combinations thereof.

8. The method according to claim 1, 2, 3 or 4 wherein the aliquots of blood fluid undergo recalcification so as to contain free calcium ions.

9. The method according to any of claim 1, 2, 3 or 4 wherein the procoagulant agent is selected from the group consisting of glass, glass spheres, glass wool, kaolin, ceramic, cotton, ellagic acid and combinations thereof.

10. The method according to any of claim 1, 2, or 4 further comprising extracting thrombin serum by withdrawing a plunger of a syringe.

11. The method according to claim 3 wherein the extraction of extracting thrombin serum supplemented with ethanol is performed by withdrawing the plunger of a syringe.

12. The method according to any of claim 2, 3 or 4 wherein said activated procoagulant agent is stored for a time period of between about 1 minute to 10 hours.

13. The method according to any of claim 2, 3 or 4 wherein the activated procoagulant is used repetitively with additional blood fluid aliquots to yield thrombin serum upon demand.

14. The method according to any of claim 3 or 4 wherein trituration of said fibrin gel is performed one or more times.

15. The method according to any of claim 3 or 4 wherein trituration of said fibrin gel is performed by mechanical agitation.

* * * * *